(12) United States Patent
Walt et al.

(10) Patent No.: US 7,115,884 B1
(45) Date of Patent: Oct. 3, 2006

(54) SELF-ENCODING FIBER OPTIC SENSOR

(75) Inventors: David R. Walt, Lexington, MA (US);
Todd A. Dickinson, Medford, MA (US)

(73) Assignee: Trustees of Tufts College, Boston, MA (US)

( * ) Notice: Subject to any disclaimer, the term of this patent is extended or adjusted under 35 U.S.C. 154(b) by 981 days.

(21) Appl. No.: 08/944,850

(22) Filed: Oct. 6, 1997

(51) Int. Cl.
*G01N 21/64* (2006.01)

(52) U.S. Cl. .................................... 250/459.1
(58) Field of Classification Search ............... 250/459.1
See application file for complete search history.

(56) References Cited

U.S. PATENT DOCUMENTS

| | | | |
|---|---|---|---|
| 4,200,110 A | 4/1980 | Peterson et al. |
| 4,499,052 A | 2/1985 | Fulwyler |
| 4,682,895 A | 7/1987 | Costello |
| 4,785,814 A | 11/1988 | Kane |
| 4,822,746 A | 4/1989 | Walt |
| 4,824,789 A | 4/1989 | Yafuso et al. |
| 4,999,306 A | 3/1991 | Yafuso et al. |
| 5,002,867 A | 3/1991 | Macevicz |
| 5,028,545 A | 7/1991 | Soini |
| 5,105,305 A | 4/1992 | Betzig et al. |
| 5,114,864 A | 5/1992 | Walt |
| 5,132,242 A | 7/1992 | Cheung |
| 5,143,853 A | 9/1992 | Walt |
| 5,194,300 A | 3/1993 | Cheung |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,302,509 A | 4/1994 | Cheeseman |

(Continued)

FOREIGN PATENT DOCUMENTS

EP         0269764         6/1988

(Continued)

OTHER PUBLICATIONS

Drmanac, R. et al., "Sequencing by Oligonucleotide Hybridization: A Promising Framework in Decoding of The Genome Program," The First International Conference on Electrophoresis, Supercomputing and the Human Genome, Proceeding of the Apr. 10-13, 1990 Conference at Florida State University. Ed. C. Cantor and H. Lim.

(Continued)

*Primary Examiner*—Constantine Hannaher
(74) *Attorney, Agent, or Firm*—Dorsey & Whitney LLP; Robin M. Silva

(57) ABSTRACT

Self-encoding microspheres having distinct characteristic optical response signatures to specific target analytes may be mixed together while the ability is retained to identify the sensor type and location of each sensor in a random dispersion of large numbers of such sensors in a sensor array using an optically interrogatable encoding scheme, resulting in a microsphere-based analytic chemistry system. Individual microsphere sensors are disposed in microwells at a distal end of a fiber bundle and are optically coupled to discrete fibers or groups of fibers within the bundle to form an optical fiber bundle sensor. The identities of the individual sensors in the array are self-encoded by exposing the array to a reference analyte while illuminating the array with excitation light energy. A single sensor array may carry thousands of discrete sensing elements whose combined signal provides for substantial improvements in sensor detection limits, response times and signal-to-noise ratios.

10 Claims, 18 Drawing Sheets

U.S. PATENT DOCUMENTS

| | | | |
|---|---|---|---|
| 5,308,771 A | 5/1994 | Zhou et al. |
| 5,320,814 A | 6/1994 | Walt et al. |
| 5,357,590 A | 10/1994 | Auracher |
| 5,380,489 A | 1/1995 | Sutton et al. |
| 5,435,724 A | 7/1995 | Goodman et al. |
| 5,474,895 A | 12/1995 | Ishii et al. |
| 5,481,629 A | 1/1996 | Tabuchi |
| 5,494,798 A | 2/1996 | Gerdt et al. |
| 5,494,810 A | 2/1996 | Barany et al. |
| 5,496,997 A | 3/1996 | Pope |
| 5,512,490 A | 4/1996 | Walt et al. |
| 5,516,635 A | 5/1996 | Ekins et al. |
| 5,518,883 A | 5/1996 | Soini |
| 5,565,324 A | 10/1996 | Still et al. |
| 5,573,909 A | 11/1996 | Singer et al. |
| 5,575,849 A | 11/1996 | Honda et al. |
| 5,633,972 A | 5/1997 | Walt et al. |
| 5,639,603 A | 6/1997 | Dower et al. |
| 5,656,241 A | 8/1997 | Seifert et al. |
| 5,679,524 A | 10/1997 | Nikiforov et al. |
| 5,690,894 A | 11/1997 | Pinkel et al. |
| 5,814,524 A | 9/1998 | Walt et al. |
| 5,830,711 A | 11/1998 | Barany et al. |
| 5,837,196 A | 11/1998 | Pinkel et al. |
| 5,840,256 A | 11/1998 | Demers et al. |
| 5,854,684 A | 12/1998 | Stabile et al. |
| 5,856,083 A | 1/1999 | Chelsky et al. |
| 5,858,732 A | 1/1999 | Solomon et al. |
| 5,863,708 A | 1/1999 | Zanzucchi et al. |
| 5,866,331 A * | 2/1999 | Singer et al. ............... 435/6 |
| 5,888,723 A | 3/1999 | Sutton et al. |
| 5,900,481 A | 5/1999 | Lough et al. |
| 6,013,456 A | 1/2000 | Akgavan-Tafti |
| 6,023,540 A | 2/2000 | Walt et al. |
| 6,027,889 A | 2/2000 | Barany et al. |
| 6,051,380 A | 4/2000 | Sosnowski et al. |
| 6,054,564 A | 4/2000 | Barany et al. |
| 6,083,763 A | 7/2000 | Balch |
| 6,110,678 A | 8/2000 | Weisburg et al. |
| 6,172,218 B1 | 1/2001 | Brenner |
| 6,251,639 B1 | 6/2001 | Kurn |
| 6,268,148 B1 | 7/2001 | Barany et al. |

FOREIGN PATENT DOCUMENTS

| | | |
|---|---|---|
| EP | 0 392 546 | 10/1990 |
| EP | 0478 319 | 4/1992 |
| EP | 0 723 146 | 7/1996 |
| GB | 2 294 319 | 4/1996 |
| WO | 89/11101 | 11/1989 |
| WO | 93/02360 | 2/1993 |
| WO | WO 93/25563 A1 | 12/1993 |
| WO | 94/12863 | 6/1994 |
| WO | 96/03212 | 2/1996 |
| WO | 97/12030 | 4/1997 |
| WO | 97/14028 | 4/1997 |
| WO | 97/14928 | 4/1997 |
| WO | WO 97/31256 A3 | 8/1997 |
| WO | 97/40385 | 10/1997 |
| WO | WO 98/13523 | 4/1998 |
| WO | 98/40726 | 9/1998 |
| WO | 98/50782 | 11/1998 |
| WO | 98/53093 | 11/1998 |
| WO | 98/53300 | 11/1998 |
| WO | 99/18434 | 4/1999 |
| WO | WO 99/60170 | 11/1999 |
| WO | 99/67414 | 12/1999 |
| WO | WO 99/67641 | 12/1999 |
| WO | WO 00/04372 | 1/2000 |
| WO | WO 00/13004 | 3/2000 |
| WO | WO 00/16101 | 3/2000 |
| WO | WO 00/39587 | 7/2000 |
| WO | WO 00/47996 | 8/2000 |
| WO | WO 00/58516 A2 | 10/2000 |
| WO | WO 00/63437 | 10/2000 |
| WO | WO 00/71243 | 11/2000 |
| WO | WO 00/71995 | 11/2000 |
| WO | WO 00/75373 | 12/2000 |

OTHER PUBLICATIONS

U.S. Appl. No. 08/818,199, filed Mar. 1997, Walt et al.
U.S. Appl. No. 08/851,023, filed May 1997, Walt et al.
U.S. Appl. No. 08/818,199, filed Mar. 1997, Walt et al.
U.S. Appl. No. 08/851,203, filed May. 1997, Walt et al.
Anonymous, "Fluorescent Microspheres," Tech. Note 19, Bang Laboratories, (Fishers, In) Feb. 1997.
Anonymous, "Microsphere Selection Guide," Bangs Laboratories, (Fisher, In) Sep. 1998.
Bangs, L.B., "Innumological Applications of Microspheres," The Latex Course, Bangs Laboratories (Carmel, IN) Apr. 1996.
Healey, B., et al. "Development of a Penicillin Biosensor Using a Single Optical Imaging Fiber," SPIE 2388:568-573 (1995).
Healey, B., et al. "Improved Fiber-Optic Chemical Sensor for Penicillin," Analytical Chemistry, 67(24): 4471-4476 (1995).
Michael, K., et al. "Fabrication of Micro- and Nanostructures Using Optical Imaging Fibers and Their Use as Chemical Sensors," Electrochemical Society Proceedings 97-5: 153-158 (1997).
Pantoano, P. et al., "Ordered nanowell Arrays," Chem. Mater., 8:2832-2835 (1996).
Peterson, J. et al., "Fiber Optic pH Probe for Physiological Use," Anal. Chem., 52:864-869 (1980).
Pope, E. "Fiber Optic Chemical Microsensors Employing Optically Active Silica Microspheres," SPIE, 2388:245-256 (1995).
Walt, D. "Fiber-Optic Sensors for Continuous Clinical Monitoring," Proceedings of the IEEE, 80(6):903-911 (1992).
Ferguson, J. et al. "a Fiber-Optic DNA BiosensorMicroarray for the Analysis of Gene Expression," Nature Biotechnology, 14:1681-1684 (1996).
Healey, B. et al. "Fiberoptic DNA Sensor Array Capable of Detecting Point Mutations," Analytical Biochemistry, 251:270-279 (1997).
Piunno, P. et al. "Fiber-Optic DNA Sensor for Fluorometric Nucleic Acid Determination," Anal. Chem. 67:2635-2643 (1995).
Abel, A. et al. "Fiber-Optic Evanescent Wave Biosensor for the Detection of Oligonucleotides," Anal. Chem. 68:2905-2912 (1996).
Strachan, N.J.C. et al. "A Rapid General Method for the Identification of PCR Products Using a Fibre-Optic Biosensor and its Application to the detection of *Listeria*," Letters in Applied Microbiology, 21:5-9 (1995).
Barnard et al., "A Fibre-Optic Chemical Sensor with Discrete Sensing Sites," Nature, 353:338-340 (Sep. 26, 1991).
Fuh, et al., "Single Fibre Optic Fluorescence pH Probe," Analyst, 112:1159-1163 (1987).
Hirschfeld, et al., "Laser-Fiber-Optic "Optrode" for Real Time In Vivo Blood Carbon Dioxide Level Monitoring," Journal of Lightwave Technology, LT-5(7):1027-1033 (Jul. 1987).
Mignani, et al., "In-Vivo Biomedical Monitoring by Fiber-Optic Systems," Journal of Lightwave Technology, 13(7):1396-1406 (1995).
Peterson, et al., "Fiber-Optic Sensors for Biomedical Applications," Science, 13:123-127 (1984).
Michael et al., "Randomly Ordered Addressable High-Density Optical Sensor Arrays," Anal. Chem. 70(7):1242-1248 (Apr. 1998).
Chen et al., "A Microsphere-Based Assay for Multiplexed Single Nucleotide Polymorphism Analysis Using Single Base Chain Extension," Genome Research, 10(4):549-557 (Apr. 2000).
Czarnik, "Illuminating the SNP Genomic Code," Modern Drug Discovery, 1(2): 49-55 (Nov./Dec. 1998).
Drmanac, R. et al., "Prospects for a Miniaturized, Simplified and Frugal Human Genome Project," Scientia Yugoslavica, 16(1-2):97-107 (1990).

Drmanac, R. et al., "Sequencing by Hybridization (SBH) with Oligonucleotide Probes as an Integral Approach for the Analysis of Complex Genomes," International Journal of Genome Research, 1(1):59-79 (1992).

Drmanac, R. et al., "Sequencing by Hybridization," Automated DNA Sequencing and Analysis, ed. M. Adams, C. Fields and J. Venter. (1994).

Iannone et al., "Multiplexed Single Nucleotide Polymorphism Genotyping by Oligonucleotide Ligation and Flow Cytometry," Cytometry, 39:131-140 (Feb. 1, 2000).

Lyamichev et al., "Polymorphism indentification and quantitative detection of genomic DNA by invasive cleavage of oligonucleotide probes," Nature Biotechnology, 17:292-296 (Mar. 1999).

Michael et al., "Making Sensors out of Disarray: Optical Sensor Microarrays," Proc. SPIE, 3270: 34-41 (may 1998).

Walt, D. "Fiber Optic Imaging Sensors," Accounts of Chemical Research, 31(5): 267-278 (May 1998).

* cited by examiner

BEFORE TAPPING

AFTER TAPPING

PS802 648.C

AIR

TOLUENE

POLY METHYL STYRENE /
2% DIVINYL BENZENE

AIR

TOLUENE

POLY METHYL STYRENE

AIR

TOLUENE

SELF-ENCODING FIBER OPTIC SENSOR

This invention was made with government support under N00014-94-1-0312 awarded by the Department of the Navy, Office of Naval Research. The government has certain rights in the invention.

FIELD OF THE INVENTION

The present invention is generally concerned with chemical sensors, sensor arrays and sensing apparatus for the detection of gaseous and liquid analytes. More particularly, the invention is directed to optical chemical sensors and the detection and evaluation of optical data generated by sensing receptor units.

BACKGROUND OF THE INVENTION

The use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in *C.R.C. Critical Reviews In Analytical Chemistry*, Vol. 19, 1988, pp. 135–173; Wolfbeis, O. S., "Fiber Optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2(4):38 (1987); Walt, et al., "Chemical Sensors and Microinstrumentation", *ACS Symposium Series*, Vol. 403, 1989, p. 252, and Wolfbeis, O. S., *Fiber Optic Chemical Sensors*, Ed. CRC Press, Boca Raton, Fla., 1991, 2nd Volume.

When using an optical fiber in an in vitro/in vivo sensor, one or more light absorbing dyes are located near its distal end. Typically, light from an appropriate source is used to illuminate the dyes through the fiber's proximal end. The light propagates along the length of the optical fiber; and a portion of this propagated light exits the distal end and is absorbed by the dyes. The light absorbing dye may or may not be immobilized; may or may not be directly attached to the optical fiber itself; may or may not be suspended in a fluid sample containing one or more analytes of interest; and may or may not be retainable for subsequent use in a second optical determination.

Once the light has been absorbed by the dye, some light of varying wavelength and intensity returns, conveyed through either the same fiber or collection fiber(s) to a detection system where it is observed and measured. The interactions between the light conveyed by the optical fiber and the properties of the light absorbing dye provide an optical basis for both qualitative and quantitative determinations.

Of the many different classes of light absorbing dyes which conventionally are employed with bundles of fiber strands and optical fibers for different analytical purposes are those more common compositions that emit light after absorption termed "fluorophores" and those which absorb light and internally convert the absorbed light to heat, rather than emit it as light, termed "chromophores."

Fluorescence is a physical phenomenon based upon the ability of some molecules to absorb light (photons) at specified wavelengths and then emit light of a longer wavelength and at a lower energy. Substances able to fluoresce share a number of common characteristics: the ability to absorb light energy at one wavelength; reach an excited energy state; and subsequently emit light at another light wavelength. The absorption and fluorescence emission spectra are individual for each fluorophore and are often graphically represented as two separate curves that are slightly overlapping. The same fluorescence emission spectrum is generally observed irrespective of the wavelength of the exciting light and, accordingly, the wavelength and energy of the exciting light may be varied within limits; but the light emitted by the fluorophore will always provide the same emission spectrum. Finally, the strength of the fluorescence signal may be measured as the quantum yield of light emitted. The fluorescence quantum yield is the ratio of the number of photons emitted in comparison to the number of photons initially absorbed by the fluorophore. For more detailed information regarding each of these characteristics, the following references are recommended: Lakowicz, J. R., *Principles of Fluorescence Spectroscopy*, Plenum Press, New York, 1983; Freifelder, D., Physical Biochemistry, second edition, W. H. Freeman and Company, New York, 1982; "Molecular Luminescence Spectroscopy Methods and Applications: Part I" (S. G. Schulman, editor) in *Chemical Analysis*, vol. 77, Wiley & Sons, Inc., 1985; *The Theory of Luminescence*, Stepanov and Gribkovskii, Iliffe Books, Ltd., London, 1968.

Many of the recent improvements employing optical fiber sensors in both qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations and applications such as pH measurement, oxygen detection, and carbon dioxide analyses. These developments are exemplified by the following publications: Freeman, et al., *Anal Chem.* 53:98 (1983); Lippitsch et al., *Anal. Chem. Acta.* 205:1, (1988); Wolfbeis et al., *Anal. Chem.* 60:2028 (1988); Jordan, et al., *Anal. Chem.* 59:437 (1987); Lubbers et al., *Sens. Actuators* 1983; Munkholm et al., *Talanta* 35:109 (1988); Munkholm et al., *Anal. Chem.* 58:1427 (1986); Seitz, W. R., *Anal. Chem.* 56:16A-34A (1984); Peterson, et al., *Anal. Chem.* 52:864 (1980): Saari, et al., *Anal. Chem.* 54:821 (1982); Saari, et al., *Anal. Chem.* 55:667 (1983); Zhujun et al., *Anal. Chem. Acta.* 160:47 (1984); Schwab, et al., *Anal. Chem.* 56:2199 (1984); Wolfbeis, O. S., "Fiber Optic Chemical Sensors", Ed. *CRC Press, Boca Raton, Fla.,* 1991, 2nd Volume; and Pantano, P., Walt, D. R., *Anal. Chem.,* 481A–487A, Vol. 67, (1995).

More recently, fiber optic sensors have been constructed that permit the use of multiple dyes with a single, discrete fiber optic bundle. U.S. Pat. Nos. 5,244,636 and 5,250,264 to Walt, et al. disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

Most recently, fiber optic sensors have been employed in arrays of semi-selective chemical sensors and pattern recognition schemes to discriminate and quantify odors. Such approaches have been useful in implementing the principles of biological olfaction in the design of sensing devices or systems. In this field of biomimetry, various technologies have been applied to the sensor transduction mechanism. For example, surface acoustic wave, conducting polymer, metal oxide sensor field-effect transistor (MOSFET), piezoelectric, and quartz crystal microbalance sensor arrays have been pursued.

While such technologies provide inventive approaches utilizing a variety of physical and chemical phenomena to odor sensing, there are a number of limitations to these methods which restrict the efficacy of such devices. Firstly, element-to-element reproducibility both within a single array and between sensor arrays is typically unsatisfactory and thus requires recalibration and network retraining from sensor to sensor. Secondly, most of these methods have a relatively slow response time, frequently requiring several minutes to respond to the presence of an odor. Thirdly, such methods have relatively high detection limits and low sensitivity, typically not functioning at odor levels below 10 parts per million (ppm): Fourthly, devices which embody such technologies typically require a relatively large inherent size, thereby restricting miniaturization of the sensor array for use in remote sensing applications. Finally, construction of multi-sensor arrays by these methods is complex and involves expensive and tedious preparation and placement of individual sensors within a well-defined array.

Most recently, many of these shortcomings have been overcome through the application of fiber optic sensor arrays in an artificial nose sensor device and system. U.S. Pat. Nos. 5,320,814 and 5,512,490 to Walt, et al., the teachings of each of these patents being incorporated herein by reference, disclose a fiber optic array formed of heterogeneous, semi-selective thin films which function as sensing receptor units and are able to detect a variety of different analytes and ligands using spectral recognition patterns. This technology has been applied to a vapor-sensing system which utilizes arrays of polymer-dye combinations which coat the ends of select optical fibers in a fiber optic bundle. These developments are further described in Dickinson, et al, *Nature* 382:697 (1996) and White, et al, *Anal. Chem.* 68:2191 (1996).

An innovative feature of the four previously referenced patents to Walt, et al., was the placement of multiple chemical functionalities at the end of a single optical fiber bundle sensor. This configuration yielded an analytic chemistry sensor that could be remotely monitored via the typically small bundle. The drawback, however, was the difficulty in applying the various chemistries associated with the chemical functionalities at the sensor's end; the functionalities were built on the sensor's end in a step-wise serial fashion. This was a slow process, and in practice, only tens of functionalities could be applied.

U.S. patent application Ser. No. 08/818,199 to Walt, et al, the teachings of which are incorporated herein by this reference, discloses the use of dye infiltrated polymer microspheres as a substitute for polymer-dye coating layers in optical fiber array sensors. With this approach, a fiber optic bundle serves as a substrate for dye-polymer microsphere array which contains a variety of microsphere bead sensors having different chemical and optical responses to the presence of target analytes. One innovative feature of this invention is in providing for a bead-based analytic chemistry system in which beads or microspheres carrying different chemical functionalities may be mixed together while retaining the ability to identify the functionality of each bead using an optically interrogatable encoding scheme. Additionally, this invention provides for an optical fiber bundle sensor in which the separate beads or microspheres may be optically coupled to discrete fibers or groups of fibers within the bundle. While the innovative features of this invention have separate applications, when implemented together, the invention provides for an optical fiber sensor that can support large numbers, thousands or more, of separate chemical sensor elements, which can be incorporated into a chemical sensor array and chemical analysis system. This approach provides for rapid fabrication and assembly of individual sensors and complex sensor arrays containing a multitude of discrete sensor types. The method also provides for a high degree of reproducibility and conformity within a batch of sensors and sensor arrays. Additional advantages are realized due to the ultrafine sizing available in microspheres. The overall size of the sensor array can be substantially reduced to submillimeter scale. This reduction in scale is particularly advantageous for remote sensing arrays.

While the method of applying microsphere sensor elements in chemical sensor arrays as taught in U.S. patent application Ser. No. 08/818,199 to Walt, et al, has many innovative features, this method has certain limitations. The method requires a complex multi-step bead encoding process to identify the type and location of bead subpopulations used in the sensor array. Beads are encoded by employing combinations of fluorescent dyes in varying ratio. The choice of encoding dyes is limited to those dyes which emit light at different wavelengths upon exposure to excitation light energy. While combinations of dyes in different ratios provide for encoding subpopulations of beads, the number of dye ratios available for encoding beads with a given dye pair or combination is significantly limited due to crowding the emission spectrum from peak overlap. In addition, a separate reporting dye is necessary for obtaining a unique characteristic optical response signature for a target analyte. Thus, the encoding dye choice is further limited by selecting dyes whose emission wavelengths do not overlap or interfere with the reporting dye which is uniquely responsive to the presence of an analyte.

Another limiting feature of this invention is that the process of encoding beads requires a series of measurements which calibrate and train the sensors and the sensor array. Encoding is initially accomplished by first illuminating the beads with excitation light energy and monitoring and recording the type and location of the specific bead subpopulation within the sensor array having a given encoding dye ratio. Next, the array is exposed to an analyte while illuminating the array with excitation light energy in the presence of a reporter dye. Those beads which are responsive to the analyte in the presence of the reporter dye are monitored and mapped on the sensor array. In addition, the characteristic optical response signature is stored in a library. This step is repeated for each analyte of interest in combination with a reporter dye. Once all bead subpopulations are encoded and their response characteristics monitored and recorded, the entire sensor array must be decoded for each analyte by indexing each sensor element with the stored optical response signature for each analyte. This process of decoding individual subpopulations of beads may be require additional steps when a large number of subpopulations are deployed in the array, thereby increasing the training time required for each array.

Other alternative approaches to bead encoding, utilizing molecular tagging, capillary gas chromatography and electron capture detection have been disclosed by Still, et al, *Acc. Chem. Res.* 29:155 (1996). However, such methods are limited in scope and have been applied only to a narrow class of bead materials having specific chemical functionality and molecular tags which are readily analyzable.

SUMMARY OF THE INVENTION

In general, the invention provides for an analytic chemistry system that comprises a self-encoding sensor array comprising a population of beads or microspheres. Within the bead population are separate bead subpopulations, each of which provides a characteristic optical response signature when illuminated by excitation light energy in the presence of a targeted analyte. Although the subpopulations may be randomly mixed together, the identity and location of each bead is determined via a characteristic optical response signature when illuminated by excitation light energy in the presence of a reference analyte. As a result, by comparing the response of the entire sensor array to a known analyte, the individual sensor elements of the array are conveniently decoded simultaneous in one simple measurement. In subsequent measurements of unknown analytes, the optical response of each element in the array can be compared to a library of characteristic optical response signatures for its corresponding bead subpopulation type, where the characteristic optical response signature to various analytes has been previously measured and recorded, and either the identity of the unknown can be determined or the sensor array can be trained to associate the measured response with a particular analyte which is then added to the library of response signatures.

The present invention overcomes certain limitations of the current art by embodying the innovation of a self-encoding sensor array wherein a characteristic optical response signature is produced by the interaction of specific bead subpopulation compositions with a reporter dye. The self-encoding feature of the present invention eliminates the need for a more complex, multi-step encoding system. In the self-encoding sensor array of the present invention, the response signal to a target analyte serves both as a response signature for the target analyte and as the encoding signal for the entire sensor array and subpopulations within the array. The decoding of the array is thus accomplished in a one-step process during the array response measurement of a target analyte and utilizes the very response which is used to identify the target analyte. The bead encoding is thus incorporated into the array by the nature of the bead subpopulation responses to target analytes.

In the present invention, each bead-dye combination of a subpopulation has a characteristic optical response signature when exposed to a given vapor. The self-encoding concept is provided by the unique response characteristics of the dye in combination with a specific bead matrix material. Thus the bead subpopulations which are randomly dispersed in a sensor array can be rapidly identified and located after placement in the array simply by exposing the sensor array to a known test vapor and matching the resulting optical response signature to those obtained for each bead subpopulation. With this approach, the beads are self encoding and the response characteristics of the entire sensor array are rapidly determined and stored for measurement of a target analyte. The method of the present invention is particularly useful in applications of sensor arrays containing thousands of sensors having distinctive optical response signature characteristics.

The present invention embodies a bead-based analytical chemistry system in which beads or microspheres are fabricated from various inorganic or organic materials wherein each material can be identified by a characteristic temporal optical response signature which enables verifying both the identity and location of a particular bead within a sensor array upon exposure to a reference analyte while illuminating with excitation light energy. The invention provides for utilization of any source of excitation light energy and is not limited to a specific wavelength. The principal requirement of the excitation light is that it produces emitted light of a characteristic wavelength upon illumination of a reporter dye associated with a given bead composition.

In a preferred embodiment of the present invention, ultra-fine, porous microbeads or microspheres are utilized as individual sensors. The utilization of porous micrometer scale sensors provides for improved sensor response and sensitivity. The reduction in sensor dimension substantially reduces the diffusion length and time for analyte interaction with individual sensors and significantly shortens the sensor response time, while simultaneously enhancing sensor sensitivity and lowering detection limits.

In another preferred embodiment of the present invention, the sensor array is comprised of subpopulations of beads or microspheres which are disposed on a distal end of an optical fiber bundle wherein the separate beads or microspheres may be optically coupled to discrete fibers or groups of fibers within the bundle. Since typically, such fiber optic bundles comprise thousands of discrete fibers, the present invention thus provides for an optical fiber sensor which can support a large number, thousands or more, of sensor array elements of distinct and varying subpopulations each having a characteristic optical response signature when exposed to an analyte while being illuminated by excitation light energy.

In one preferred embodiment, the distal end of a fiber optic bundle substrate is chemically etched so as to create a cavity or micro-well at the end of a discrete fiber. In the preferred embodiment, each one of the beads is located within separate microwells formed at terminal ends of optical fibers of the bundle. These microwells are formed by anisotropic etching of the cores of the optical fibers with respect to the cladding. The resultant etched cavity is dimensioned for accommodating an individual microbead sensor and for providing optical coupling of the individual bead sensor with the discrete optical fiber in the fiber bundle. Since typical fiber optic bundles contain thousands of discrete fibers, this embodiment provides for the individual optical coupling of thousands of sensors in a sensor array, thereby providing for a large number of independent sensor measurements for each bead subpopulation within the array.

Due to both the large number of bead sensor subpopulations available and the correspondingly large number of sensor elements within each subpopulation, a significant innovation of the present invention is in providing for thousands of independent sensor response measurements in a single sensor array. This enables another significant innovation of the present invention by providing for the summing and amplification of the characteristic optical response signatures of multiple independent measurements taken from sensor beads within each sensor array bead subpopulation. This approach directly mimics the actual behavior of the human olfactory where the combined signals from thousands of receptor cells in each of grouping of nearly a thousand different receptor cell types found in the epithelium layer, none of which are particularly sensitive in themselves, lead to a highly amplified sensory response to odors [see J. S. Kauer, *Trends Neurosci.* 14:79–95(1991)].

The present invention thus embodies the evolutionary scent amplification process found in the human olfactory system in order to significantly enhance sensor array sensitivity to analytes by summing the low-level responses of a large number of sensor array elements. By summing the responses from several beads at low vapor concentrations, a substantial improvement in signal-to-noise ratios is achieved, exceeding a factor of ten or more. This innovation has led to reducing the detection limit of the sensor array by over an order of magnitude. The enhancement in sensitivity provided by the sensor array of the present invention is generally known to be directly proportional to the square root of the number of independent sensor bead responses available for summing. With such enhancements, detection limits approaching parts per billion are achievable.

In preferred embodiments, the sensor beads are self-encoded using a reporter dye that is preferably infiltrated or entrapped within the beads. The reporter dye may be a chromophore or phosphor but is preferably a fluorescent dye, which due to characteristically strong optical signals provide a good signal-to-noise ratio for decoding. Although not necessary, the self-encoding can also be accomplished by utilizing the ratios of two or more reporting dyes having characteristic and discrete emission peaks and measuring the peak intensity ratios upon illumination with excitation light energy.

According to another embodiment, the invention also concerns a chemical sensor array designed with a predetermined chemical specificity. In this embodiment, additional chemical functionality can be incorporated into each sensor subpopulation by attaching a desired moiety to the surfaces of the beads. In another embodiment, the sensor array has a population of beads carrying chemical functionality at, on or near, a distal end of the bundle. The ability to monitor optical signature changes associated with individual or multiple beads interacting with a target analyte is provided by optically coupling those signature changes into separate optical fibers or groups of fibers of a fiber optic bundle for transmission to the proximal end where analysis is performed either manually, by the user, or automatically, using image processing techniques.

Although each sensor is different insofar that it has a different distribution of the subpopulations of beads within its microwells, only those beads that exhibit a positive optical response or signature change to a target analyte of interest need to be decoded. Therefore, the burden is placed on the analysis rather than on sensor manufacture. Moreover, since the beads and fibers in the array can be monodisperse, the fluorescent regions arising from signal generation are extremely uniform and can be analyzed automatically using commercially available microscopy analysis software. Such image processing software is capable of defining different spectral regions automatically and counting the number of segments within each region in several seconds.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
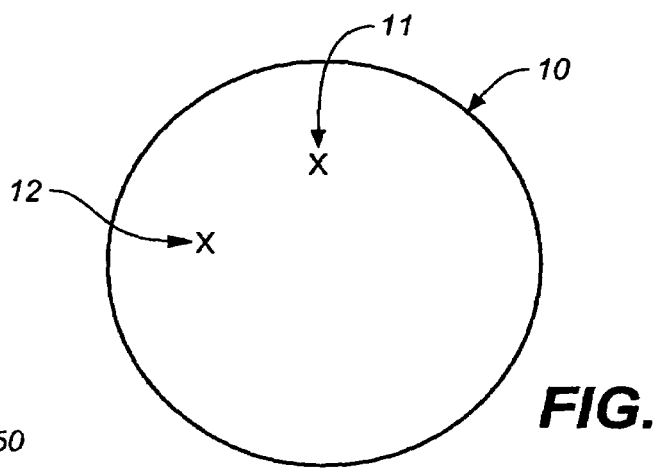
FIG. 1 is a schematic diagram illustrating the self-encoding microsphere sensor according to the present invention.

1. Microspheres:

In the following description of the preferred embodiments, the terms microsphere and bead are used interchangeably to refer to the individual sensors which comprise the sensor array elements of the present invention. FIG. 1 illustrates the construction of a typical bead or microsphere sensor 10 comprising a reporting dye 11 entrapped within bead pores 12. While both porous and non-porous beads may be utilized, porous beads are preferred for infiltrating the reporter dye and enhancing the responsivity and sensitivity of the microsphere sensor due to an increase in surface area. While spherical beads are preferred due to their uniformity in shape and size, irregular shaped beads may also be used.

Either commercially available beads may be used or beads may be fabricated from customized bead compositions using conventional bead manufacturing methods. A variety of bead materials may be utilized, ranging from porous silica, polymers, copolymers, gels, glass, plastics or ceramics, with bead sizes ranging from nanometers, e.g., 500 nm, to millimeters, e.g., 1 mm. A useful guide to commercially available bead compositions is provided in "*Microsphere Detection Guide*" from Bangs Laboratories, Fishers Ind.

Synthetic beads may be fabricated by polymerizing or copolymerizing a variety of condensation or vinyl precursor monomers or by way of combinatorial polymer synthesis. Such polymers can be further modified by the addition of plasticizers, such as tritolyl phosphate (TTP), triphenyl phospate (TTP) or dibutyl phthalate (DBP). Particularly useful dye-encoding bead candidates for use in sensor array subpopulations are polymer and copolymer materials which exhibit either a characteristic swelling upon exposure to various vapor analytes, a characteristic polarity difference due to their chemical structure, or a characteristic chemical adsorption response with various vapor analytes. In pre-screening candidate polymers as bead materials and evaluating candidates based on desirable swelling, polarity and adsorption characteristics, two particularly useful references are: R. A. McGill, et al., *Chemtech*, Sep. 24, 1996, p27–37 and J. W. Grate, et al., *Anal. Chem.* 68:913–7 (1996).

A variety of bead chemistries may be utilized in fabricating a wide diversity of sensor bead subpopulations. For example, the following compositions have been found to be particularly useful as candidate bead materials: silica, poly (ethylene glycol), polycaprolactone, poly(1,4-butylene adipate), PDPO [poly(2,6-dimethyl-1,4-phenyleneoxide)], PS078.5 [triethoxysilyl-modified polybutadiene (50% in toluene)], PS078.8 [diethoxymethylsilyl-modified polybutadiene in toluene], CPS2067 [acryloxypropylmethyl-cyclosiloxane], PS802 [(80–85%) dimethyl-(15–20%) (acryloxypropyl) methylsiloxane copolymer], PS901.5 poly (acryloxypropyl-methyl)siloxane], PS851 [(97–98%) dimethyl-(2–3%) (methacryloxypropyl)methylsiloxane copolymer], PABS [poly(acrylonitrile-butadiene-styrene)], poly(methyl methacrylate), poly(styrene-acrylonitrile 75:25), acryloxypropylmethylsiloxane-dimethylsiloxane copolymer, methylstyrene, polystyrene, acrylic polymers, and poly(methyl styrene/divinyl benzene). Other adsorbents, such as commercially available silica beads adapted with a variety of bonded phases for use in phenomenex columns, such as beads comprising C8, C18 and phenyl hexyl, are useful as sensor bead matrices. Inorganic materials such as alumina and zeolites may also be utilized. Other polymers and copolymers having distinguishable and suitable swelling behavior, polarity and chemical adsorption characteristics are also anticipated as likely bead candidate materials. Particularly useful bead candidate materials include the polymers, copolymers, and polymerized monomers listed in Table 7, Table 8 and Table 10 of U.S. Pat. No. 5,512,490 to Walt, et al, which are herein incorporated by reference. In alternative embodiments, any synthesized or commercially available bead materials may be further modified by applying either a surface treatment or coating to modify the characteristic optical response signature. For example, where porous silica beads are utilized, N-octadecyltriethyoxysilane or 3-(trimethoxysilyl)propyl methacrylate may be applied as a silanization treatment.

The choice of subpopulations used to form the sensor array elements in a particular sensor array is primarily determined based on the analytical purposes of the sensor and the specific analytes which are targeted for detection. Typically, bead subpopulations are selected based on distinguishable differences in their characteristic optical response signatures when illuminated by excitation light energy in the presence of a target analyte. In fabricating self-encoding sensor arrays, bead subpopulations are selected which have characteristic optical response signatures when infiltrated with a reporting dye and illuminated by excitation light energy in the presence of both a reference analyte and target analyte. Thus, preferred bead materials for the sensor array are preselected based on either physical or chemical differences in bead subpopulations which produce a characteristic optical response signature in the presence of the analyte when illuminated by excitation light energy.

Features such bead material polarity, chemical structure, chemical functionality, bead surface area, bead pore size, bead swelling characteristics, or chemical adsorption behavior, either separately or in combination, contribute to the characteristic optical response signature of a given bead subpopulation. In one embodiment, bead materials which are permeable or semi-permeable to vapor or liquid analytes are preferred. In another embodiment, bead materials that swell upon contact with vapor or liquid analytes are preferred. In general, bead materials which have unique polarity, structure, pore size, surface area, fuctionality or adsorption characteristics are particularly useful for sensor bead matrices of the present invention.

The selection of chemical dye indicators is equally important to the design of a fiber optic sensor array system of the present invention. In the preferred embodiment, at least one dye 11 is incorporated into the microsphere 10. In the preferred embodiment, this dye 11 acts as both an encoding dye, for identifying the bead subpopulation location in the sensor array, and a reporting dye, for detecting a target analyte of interest. In an alternative embodiment, two or more dyes may be utilized as encoding-reporter dyes. In another embodiment, at least one dye is used solely as an encoding dye and a separate dye is added during analysis as a reporting dye. In one embodiment, where two or more encoding dyes are used, the ratio of peak intensities for dye pairs may be used for encoding the bead subpopulation and a separate reporter dye may be added during analysis. In an alternative embodiment, conjugated dyes, such as acrlyoyl fluorescein and others, may be utilized where it is desirable to incorporate the dye directly into a synthesized polymer or copolymer bead material.

While the reporter dye 11 may be either a chromophore-type or a fluorophore-type, a fluorescent dye is preferred because the strength of the fluorescent signal provides a better signal-to-noise ratio when decoding. In the most preferred embodiment, polarity-sensitive dyes or solvatochromic dyes are utilized. Solvatochromic dyes are dyes whose absorption or emission spectra are sensitive to and altered by the polarity of their surrounding environment. Typically, these dyes exhibit a shift in peak emission wavelength due to a change in local polarity. Polarity changes which cause such wavelength shifts can be introduced by the bead matrix used for a particular sensor bead subpopulation or, the presence of a target analyte. The change in polarity creates a characteristic optical response signature which is useful for both encoding subpopulations of bead types and for detecting specific target analytes. One preferred solvatochromic dye, NILE RED (Eastman Kodak, Rochester, N.Y.), exhibits large shifts in its emission wavelength peak with changes in the local environment polarity. In addition, NILE RED dye is soluble in a wide range of solvents, is photochemically stable, and has a relatively strong fluorescence peak. Additional dyes which are conventionally known in the art and may be used as dyes in the present invention are those found in U.S. Pat. No. 5,512,490 to Walt, et al., of which Table 3, Table 4, Table 5, Table 6 and Table 11 are incorporated herein by reference.

Different subpopulations of bead sensing elements can be fabricated for the sensor array of the present invention by immobilizing NILE RED dye polymer matrices of varying composition. By incorporating NILE RED dye in bead subpopulations made from different polymer matrices of varying polarity, hydophobicity, pore size, flexibility and swelling tendency, unique subpopulations of sensor beads are produced that react differently with molecules of individual vapors, giving rise to different fluorescence responses when exposed to organic vapors. This results in each bead subpopulation having a characteristic optical response signature when exposed to a variety of analytes.

Figure 2:
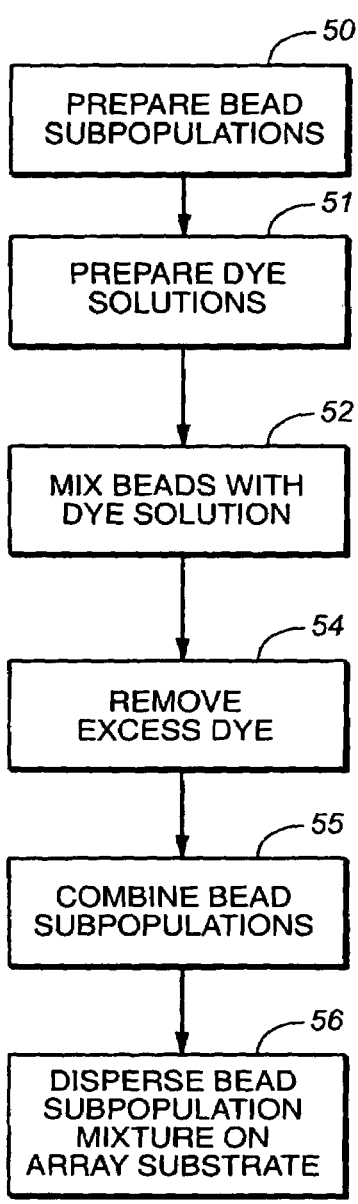
FIG. 2 is a process flow diagram of the preparation, encoding and incorporation of microspheres into a sensor array of the present invention.

FIG. 2 is a process diagram illustrating the preparation of the sensor bead subpopulations and sensor bead array. In step 50, suspensions of the various bead subpopulations are individually prepared from either commercial bead materials or synthesized bead materials which have been made from preferred polymeric materials. In this step, the beads may be prewashed, surface treated with a coupling agent, such as a silanizing solution as used in Example 2 and Example 3, or treated with a plasticizer, such as TTP, TPP or DBP as used in Example 6. In preparing the bead subpopulations, each bead grouping is typically dispersed in an appropriate solvent which may comprise additions of surfactants or dispersants to enhance dispersion. For example, TWEEN 20 detergent (J. T. Baker, Cleveland, Ohio), a polyoxyethylenesorbitan monolaurate, has been found to be particularly useful as a surfactant.

A dye solution is prepared 51 for tagging or encoding each of the bead subpopulations for subsequent identification and indexing subpopulations in the sensor array in a later decoding step. In the most preferred embodiment, a single dye serves both as a sensor bead subpopulation encoding dye and as an analyte reporting dye that is used to detect the presence of a target analyte. In another embodiment, the dye serves solely to encode the sensor bead subpopulation and an additional dye is used as a reporter dye for detection of a target analyte. In one embodiment, two or more dyes may be incorporated into the bead subpopulation and the peak intensity ratios of dye pairs may be used for encoding the sensor bead subpopulation. Typically, a single solvatochromic dye is used as both the encoding dye and reporting dye. In a preferred embodiment, NILE RED dye (Aldrich, Milwaukee, Wis.) is used. For incorporating dye into each bead subpopulation, suspensions of the beads prepared in step 50 are mixed in step 52 with dye solutions prepared in step 51. Preferably, in step 52, the beads or microspheres are placed in a dye solution comprising dye dissolved in an organic solvent that will swell the microspheres. In step 54, the beads are washed, centrifuged or filtered to remove excess dye. The microspheres are typically washed in water, methanol, or any suitable solvent that does not swell the microspheres, but in which the dyes are still soluble. This allows the residual dye to be rinsed off without rinsing the dye out of the microspheres. In an alternative embodiment, a chemical moiety or functional group may be attached to the bead surface following removal of excess dye.

In one alternative embodiment, a chemical moiety or functional group may be attached to the bead surface during this step so as to provide a particular sensor bead subpopulation with chemical specificity for targeted analytes. In an alternative embodiment, the chemical functionality may be attached to the bead at a later step 54 following removal of excess dye. Where chemical functionality is desirable, bead microspheres may be purchased with the desired chemical functionality already present. A large selection of such pre-prepared microspheres are currently available from a number of commercial vendors. Alternatively, "blank" microspheres may be used that have surface chemistries that facilitate the attachment of the desired chemical functionality by the user.

Some examples of these surface chemistries for blank microspheres are listed in Table I.

TABLE I

| Surface chemistry | Name: |
| --- | --- |
| $NH_2$ | Amine |
| COOH | Carboxylic Acid |
| CHO | Aldehyde |
| $CH_2$—$NH_2$ | Aliphalic Amine |
| CO $NH_2$ | Amide |
| $CH_2$—Cl | Chloromethyl |
| CONH—$NH_2$ | Hydrazide |
| OH | Hydroxyl |
| $SO_4$ | Sulfate |
| $SO_3$ | Sulfonate |
| Ar $NH_2$ | Aromatic Amine |

In the prior art, a large spectrum of chemical functionality have been manifest on micro spheres that produce optically interrogatable changes in the presence of a target analyte. These functionalities include basic indicator chemistry sensors, enzyme-based sensors, immuno-based sensors and gene-sensors. Examples of such useful functionalities may be found in Table II, which lists indicator chemistry sensors, Table III, which lists enzyme-based sensors, and Table IV, which lists those for gene-sensors.

TABLE II

| TARGET ANALYTE | CHEMICAL FUNCTIONALITY | NOTES ($\lambda_{ab}/\lambda_{em}$) |
|---|---|---|
| pH Sensors based on: | seminaphthofluoresceins | e.g., carboxy-SNAFL |
|  | seminaphthorhodafluors | e.g., carboxy-SNARF |
|  | 8-hydroxypyrene-1,3,6-trisulfonic acid |  |
|  | fluorescein |  |
| CO2 Sensors based On: | seminaphthofluoresceins | e.g., carboxy-SNAFL |
|  | seminaphthorhodafluors | e.g., carbody-SNARF |
|  | 8-hydroxypyrene-1,3,6-trisulfonic acid |  |
| Metal Ions Sensors based on: | desferriozamine B | e.g., Fe |
|  | cyclen derivatives | e.g., Cu, Zn |
|  | derivatized peptides | e.g., FITC-Gly-Gly-His, and FITC-Gly His, Cu, Zn |
|  | fluorexon (calcine) | e.g., Ca, Mg, Cu, Pb, Ba |
|  | calcine blue | e.g., Ca, Mg, Cu |
|  | methyl calcine blue | e.g., Ca, Mg, Cu |
|  | ortho-dianisidine tetracetic acid (ODTA) | e.g., Zn |
|  | bis-salicylidene ethylenediamine (SED) | e.g., Al |
|  | N-(6-methoxy-8-quinolyl-p-toluene-sulfonamine (TSQ) | e.g., Zn |
|  | Indo-1 | e.g., Mn, Ni |
|  | Fura-2 | e.g., Mn, Ni |
|  | Magnesium Green | e.g., Mg, Cd, Tb |
| $O_2$ | Siphenylisobenzofuran | 409/476 |
|  | Methoxyvinyl pyrene | 352/401 |
| Nitrite | diaminonaphthaline | 340/377 |
| NO | luminol | 355/411 |
|  | dihydrohodamine | 289/none |
| $Ca^{2+}$ | Bis-fura | 340/380 |
|  | Calcium Green | visible light/530 |
|  | Fura-2 | 340/380 |
|  | Indo-1 | 405/485 |
|  | Fluo-3 | visible light/525 |
|  | Rhod-2 | visible light/570 |
| $Mg^{2+}$ | Mag-Fura-2 | 340/380 |
|  | Mag-Fura-5 | 340/380 |
|  | Mag-Indo-1 | 405/485 |
|  | Magnesium Green | 475/530 |
|  | Magnesium Orange | visible light/545 |
| $Zn^{2+}$ | Newport Green | 506/535 |
| TSQ | Methoxy-Quinobyl | 334/385 |
| $Cu^+$ | Phen Green | 492/517 |
| $Na^+$ | SBFI | 339/565 |
|  | SBFO | 354/575 |
|  | Sodium Green | 506/535 |
| $K^+$ | PBFI | 336/557 |
| $Cl^-$ | SPQ | 344/443 |
|  | MQAE | 350/460 |

TABLE III

| SENSOR TARGET | CHEMICAL FUNCTIONALITY |
|---|---|
| Glucose Sensor | glucose oxidase (enz.) + $O_2$-sensitive dye (see Table I) |
| Penicillin Sensor | penicillinase (enz.) + pH-sensitive dye (see Table I) |
| Urea Sensor | urease (enz.) + pH-sensitive dye (see Table I) |
| Acetylcholine Sensor | acetylcholinesterase (enz.) + pH-sensitive dye (see Table I) |

TABLE IV

| PROBE SEQUENCES | TARGET SEQUENCES |
|---|---|
| B-glo(+) (segment of human B-globin) 5'-$NH_2$—$(CH_2)_8$-)TT TTT TTT TCA ACT TCA TCC ACG TTC ACC-3 | B-glo(+)-CF 5'-Fluorescein-TC AAC GTG GAT GAA GTT C-3' |
| IFNG (interferon gamma 1) 5'-$NH_2$—$(CH_2)_8$-$T_{12}$-TGG CTT CTC TTG GCT GTT ACT-3' | IFNG-CF 5'-Fluorescein-AG TAA CAG CCA AGA GAA CCC AAA-3' |
| IL2 (interleukin-2) 5'-$NH_2$—$(CH_2)_8$-$T_{12}$-TA ACC GAA TCC CAA ACT CAC CAG-3' | IL2-CF 5'-Fluorescein-CT GGT GAG TTT GGG ATT CTT GTA-3' |
| IL4 (interleukin-4) 5'$NH_2$—$(CH_2)_8$-$T_{12}$-CC AAC TGC TTC CCC CTC TGT-3' | IL4-CF 5'-Fluorescein-AC AGA GGG GGA AGC AGT TGG-3' |
| IL6 (interleukin-6) 5'$NH_2$—$(CH_2)_8$-$T_{12}$-GT TGG GTC AGG GGT GGT TAT T-3' | IL6-CF 5'-Fluorescein - AA TAA CCA CCC CTG ACC CAA C-3' |

Figure 3:
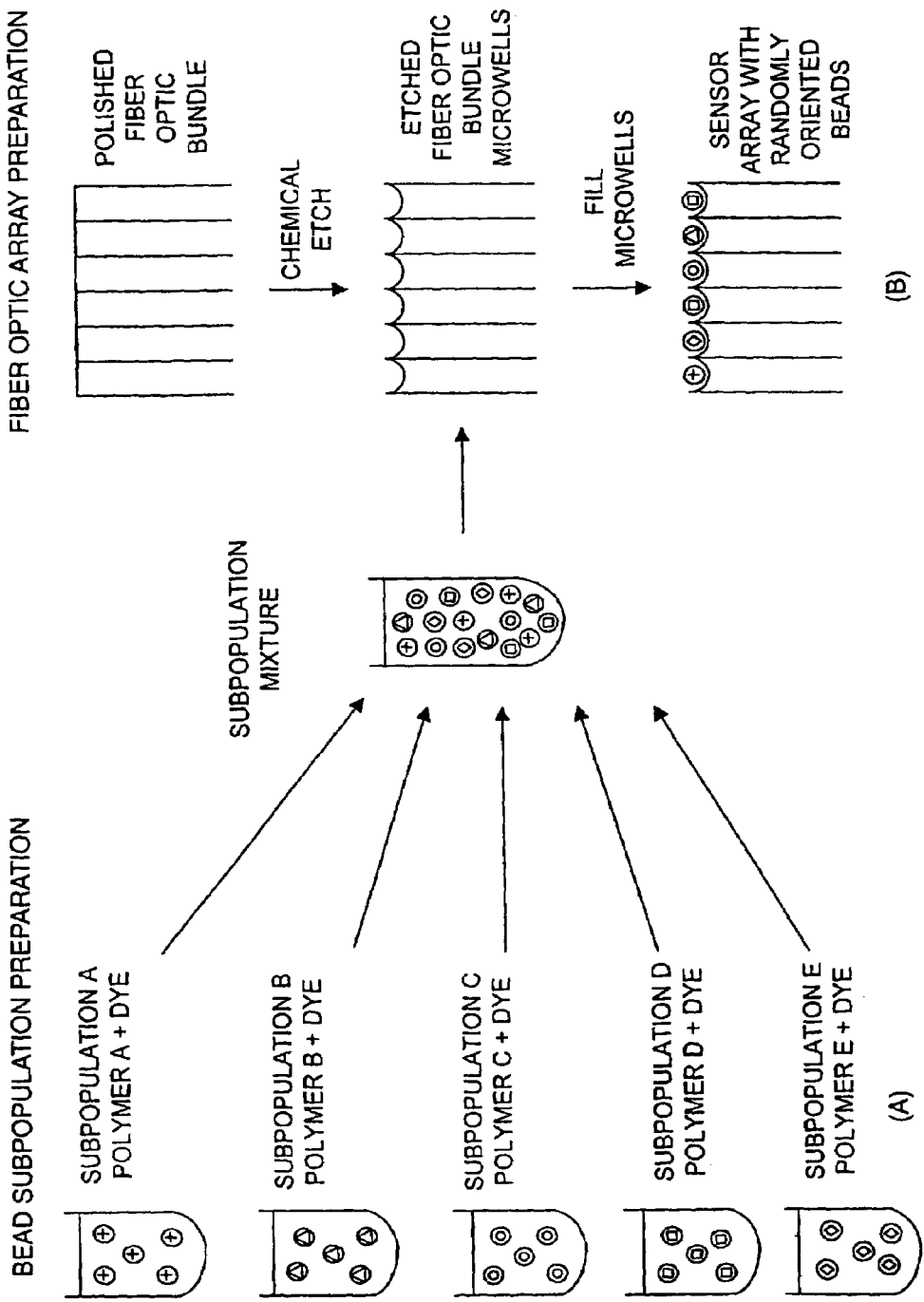
FIGS. 3A and 3B is a schematic process diagram illustrating the preparation and placement of self-encoded microsphere subpopulations in fiber optic sensor array of the present invention.

After the desired number of bead subpopulations are prepared by the method of steps 50 through 54, the subpopulations are typically combined in step 55 to provide a random mixture of subpopulations for use as sensor array elements prior to dispersing the subpopulation mixture on the array substrate in step 56. In a preferred embodiment, FIGS. 3A and 3B show a schematic process diagram which illustrates the preparation and placement of self-encoded sensor bead subpopulations in fiber optic bundle sensor array. In an alternative embodiment, step 55 (FIG. 2) may be omitted and each of the sensor bead subpopulations may be separately and sequentially positioned on the array substrate in predetermined locations.

Once the self-encoded bead subpopulations are combined and randomly positioned within a sensor array, an innovative feature of the present invention provides for rapid, simultaneous decoding of the entire sensor bead population in identifying and indexing the location of each sensor bead and each subpopulation of beads within the array.

2. Optical Fiber Sensor

Figure 7:
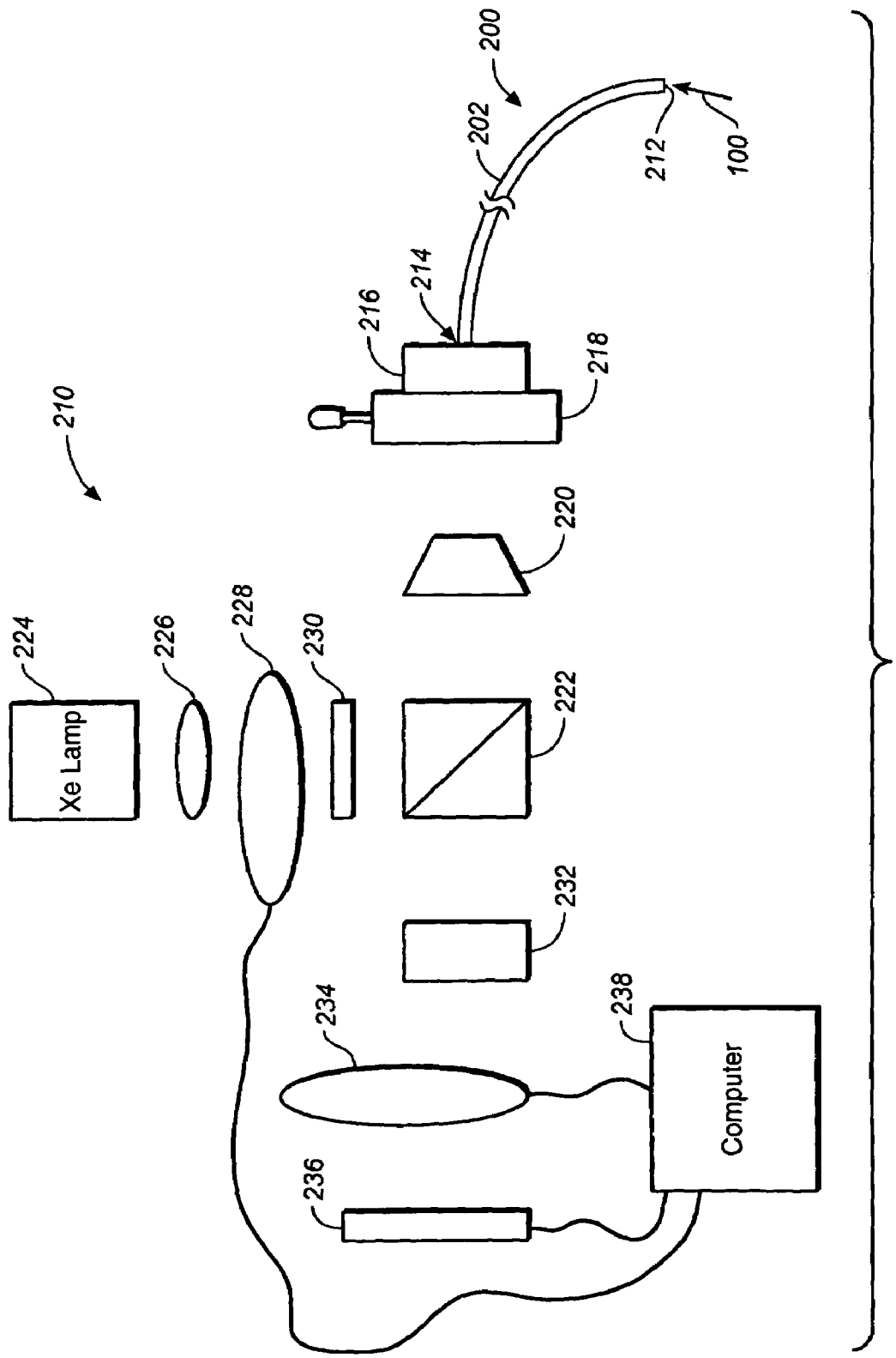
FIG. 7 is a schematic diagram of the inventive fiber optic sensor and associated instrumentation and control system.

FIG. 7 is a schematic block diagram showing the inventive optical fiber sensor 200 and associated control system 210. The fiber optic sensor 200 comprises a fiber optic bundle 202 (Galileo Electro-Optics, Sturbridge, Mass.), that is typically constructed from many thousands of separately clad discrete fibers, each only a few microns in diameter, so that light does not mix between the individual fibers. Any suitable fiber optic bundle 202 may be employed having a range in the number of individual fibers or a range of individual fiber diameters. The microsphere or bead sensor array 100 is attached to the bundle's distal end 212, with the proximal end 214 being received by a conventional z-translation microscope stage 216, for vertical positioning of the array 100 for focusing, and an x-y micropositioner 218 (Burleigh Instruments, Fishers, N.Y.), for horizontal alignment of the array 100 with the optical train. These two components act in concert to properly position the proximal end 214 of the bundle 202 for a microscope objective lens 220. Light collected by the objective lens 220 is passed to a reflected light fluorescence attachment with a four position dichromic cube wheel 222. The attachment 222 allows insertion of light from a 75 watt Xenon arc lamp 224 through the objective lens 220 to be coupled into the fiber bundle 202. The light from the source 224 is condensed by condensing lens 226, then filtered and/or shuttered by filter and shutter wheel 228.

Light returning from the distal end 212 of the bundle 202 is passed by the attachment 222 and is then shuttered and filtered by a second wheel 234. The light is then imaged on a charge coupled device (CCD) camera 236. A conventional computer 238 executes imaging processing software to process the information from the CCD camera 236 and also possibly control the first and second shutter and filter wheels 228, 234. Either a Macintosh or, alternatively, an IBM-compatible personal computer may be utilized for controlling the instrumentation and data acquisition. The instrumentation and optical apparatus deployed at the proximal end 214 of the fiber optic sensor 200, exclusive of the fiber optic sensor 200, are discussed more completely by Bronk, et al., *Anal. Chem.* 67(17):2750–2752(1995) and Bronk, et al., *Anal. Chem.* 66:3519 (1994).

The bead sensor array 100 may be attached to the distal end of the optical fiber bundle 202 using a variety of compatible processes. It is important that the microspheres 10 are located close to the end of the bundle. This ensures that the light returning in each discrete optical fiber predominantly comes from only a single microsphere. This feature is necessary to decode the self-encoded bead subpopulations for the purpose of identifying both bead type and location, to enable the interrogation of the optical signature of individual microspheres within a bead subpopulation, and to provide for the summing of individual bead responses within each subpopulation for reducing signal to noise and improving signal enhancement. The bead adhesion or affixing technique, however, must not chemically insulate the microspheres from the analyte or interfere with the optical measurement.

Figure 5A:
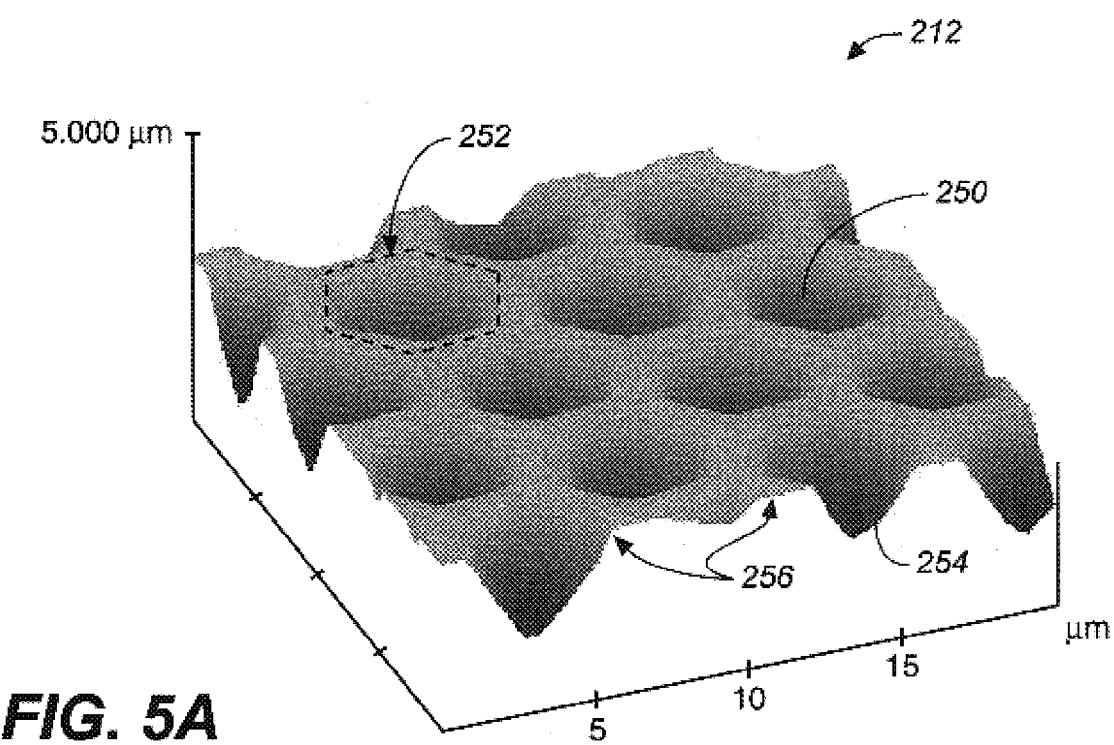
FIGS. 5A and 5B are micrographs illustrating the microwells formed on the distal end of a fiber optic bundle and microspheres inserted in the microwell cavities.
Figure 5B:
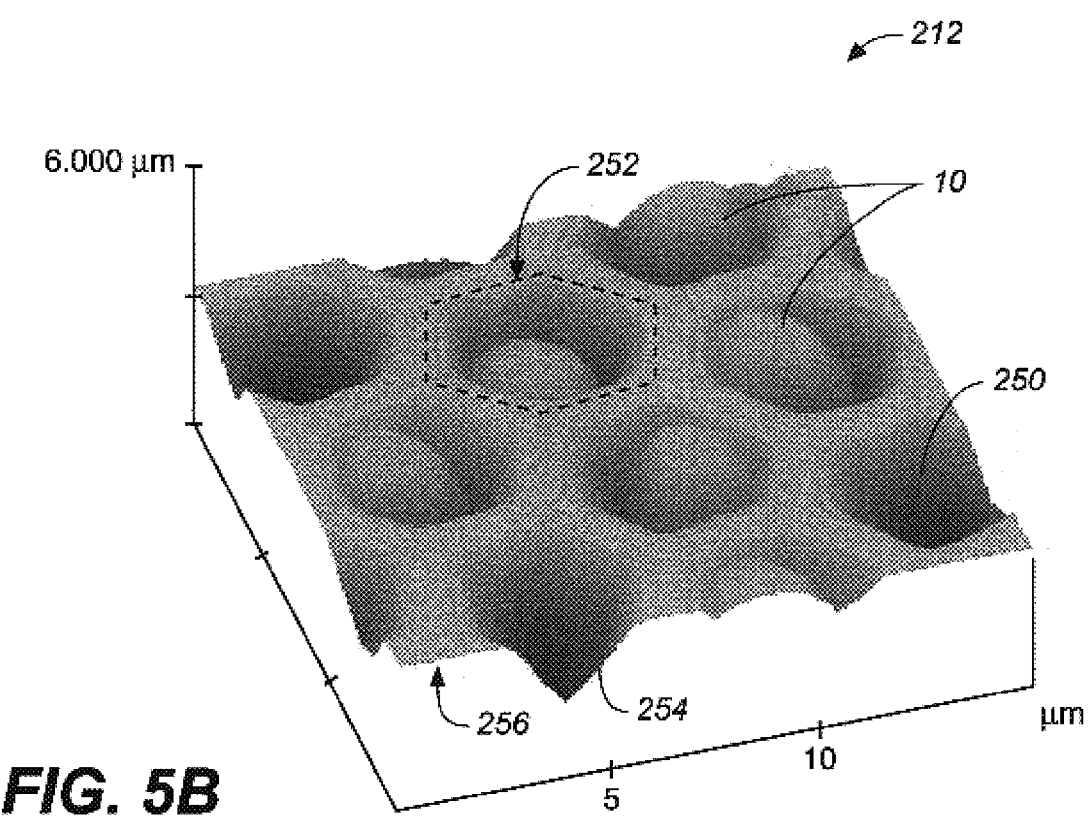

FIGS. 5A and 5B are micrographs illustrating the preferred method for attaching beads to a sensor array substrate. Microwells 250 are formed on the distal end 212 of a fiber optic bundle 202 and microspheres 10 are inserted in the microwell cavities 250. The microwells 250 are formed at the center of each optical fiber 252 of the fiber optic bundle 202. As shown in FIG. 5B, the size of the microwells 250 are coordinated with the size of the microspheres 10 so that the microspheres 10 can be placed within the microwells 250. Thus, each optical fiber 252 of the bundle 202 conveys light from the single microsphere 10 contained in its well. Consequently, by imaging the end of the bundle 202 onto the CCD array 236, the optical signatures of the microspheres 10 are individually interrogatable.

Figure 4:
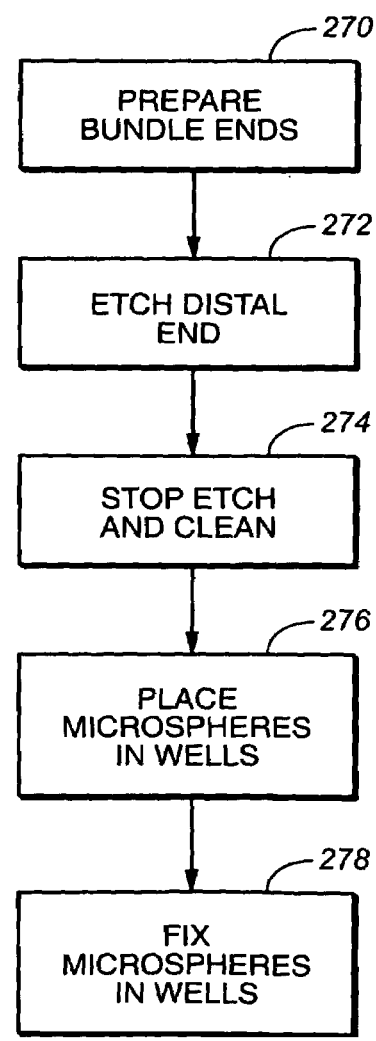
FIG. 4 is a process flow diagram illustrating microwell formation in the fiber optic bundle and placement of the microspheres in the microwells according to the method of the present invention.

FIG. 4 illustrates how the microwells 250 are formed and microspheres 10 placed in the microwells. In one embodiment, a 1 mm hexagonally-packed imaging fiber bundle 202 was employed comprising approximately 20,600 individual optical fibers having cores approximately 3.71 µm across (Part No. ET26 from Galileo Fibers, Sturbridge, Mass.). Typically, the cores of each fiber are hexagonally shaped as a result of glass hardness and drawing during fiber fabrication. In some cases, the shape can be circular, however.

In step 270, both the proximal 214 and distal 212 ends of the fiber bundle 202 are successively polished on 12 µm, 9 µm, 3 µm, 1 µm, and 0.3 µm lapping films. Subsequently, the ends can be inspected for scratches on a conventional atomic force microscope. In step 272, etching is performed on the distal end 212 of the bundle 202. A solution of 0.2 grams $NH_4F$ (ammonium fluoride) with 600 µd$H_2O$ and 100 µl of HF (hydrofluoric acid), 50% stock solution, may be used. The distal end 212 is etched in this solution for a specified time, preferably approximately 80 seconds.

Upon removal from this solution, the bundle end is immediately placed in deionized water to stop any further etching in step 274. The fiber is then rinsed in running tap water. At this stage, sonication is preferably performed for several minutes to remove any salt products from the reaction. The fiber is then allowed to air dry.

As illustrated in FIGS. 5A and 5B, the foregoing procedure produces microwells by the anisotropic etching of the fiber cores 254 favorably with respect to the cladding 256 for each fiber of the bundle 202. The microwells have approximately the diameter of the cores 254, 3.7 µm. This diameter is selected to be slightly larger than the diameters of the microspheres used, 3.1 µm, in the example. The preferential etching occurs because the pure silica of the cores 254 etches faster in the presence of hydrofluoric acid than the germanium-doped silica claddings 256.

The microspheres are then placed in the microwells 250 in step 276 according to a number of different techniques. The placement of the microspheres may be accomplished by dripping a solution containing the desired randomly mixed subpopulations of the microspheres over the distal end 212, sonicating the bundle to settle the microspheres in the microwells, and allowing the microsphere solvent to evaporate. Alternatively, the subpopulations could be added serially to the bundle end. Microspheres 10 may then be fixed into the microwells 250 by using a dilute solution of sulfonated NAFION polymer that is dripped over the end. Upon solvent evaporation, a thin film of NAFION polymer was formed over the microspheres which holds them in place. This approach is compatible for fixing microspheres for pH indication that carry FITC functionality. The resulting array of fixed microspheres retains its pH sensitivity due to the permeability of the sulfonated NAFION polymer to hydrogen ions. This approach, however, can not be employed generically as NAFION is impermeable to most water soluble species. A similar approach can be employed with different polymers. For example, solutions of polyethylene glycol, polyacrylamide, or polyhydroxymethyl methacrylate (polyHEMA) can be used in place of NAFION, polymer providing the requisite permeability to aqueous species.

In an another embodiment, an alternative fixation approach employs microsphere swelling to entrap each microsphere 10 in its corresponding microwell 250. In this approach, the microspheres are first distributed into the microwells 250 by sonicating the microspheres suspended in a non-swelling solvent in the presence of the microwell array on the distal end 212. After placement into the microwells, the microspheres are subsequently exposed to an aqueous buffer in which they swell, thereby physically entrapping them in the microwells. By way of example of this particular embodiment, one commonly known microsphere material is tentagel, a styrene-polyethylene glycol copolymer. These microspheres can be unswollen in nonpolar solvents such as hexane and swell approximately 20–40% in volume upon exposure to a more polar or aqueous media. In certain embodiments, this fixation approach may be desirable since it does not significantly compromise the diffusional or permeability properties of the microspheres themselves.

Figure 6A:
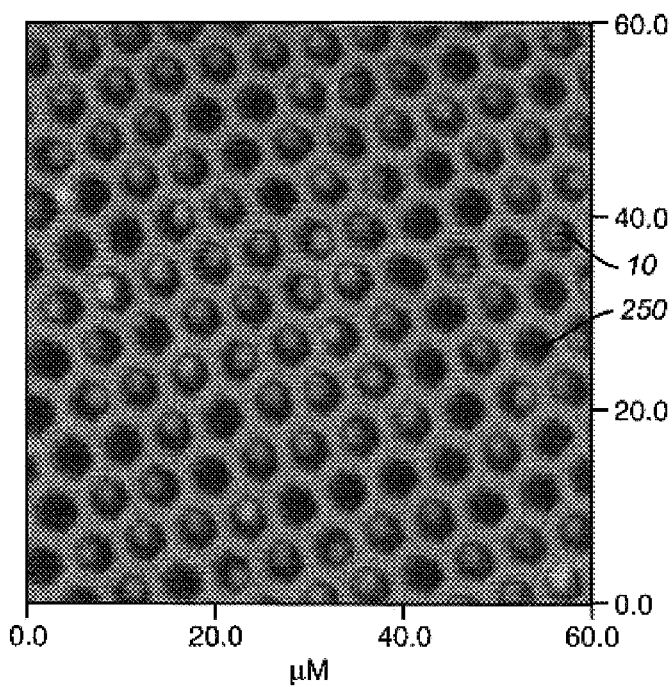
FIGS. 6A and 6B are micrographs showing the array of microspheres in their corresponding microwells prior to and subsequent to agitation by tapping and an air pulse, demonstrating the electrostatic binding of the microspheres in the microwell cavities.
Figure 6B:
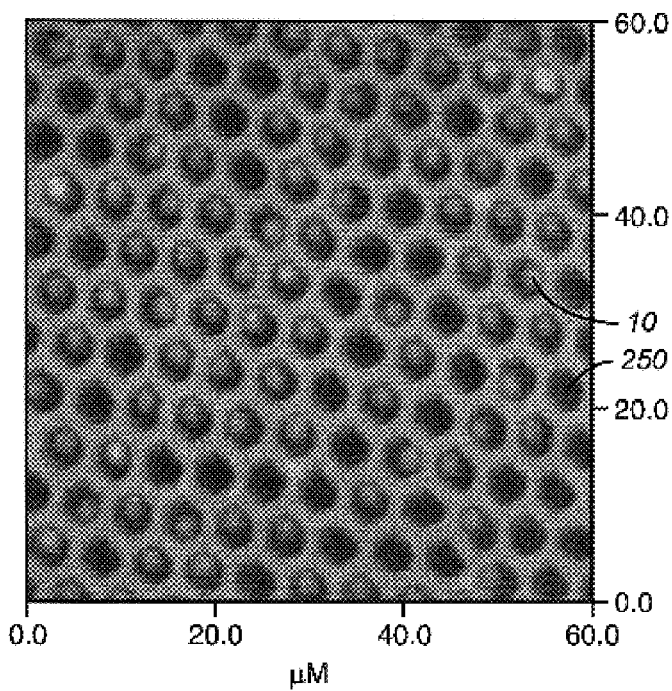

FIGS. 6A and 6B show typical microspheres 10 in microwells 250 after their initial placement and then after tapping and exposure to air pulses. FIGS. 7A and 7B illustrate that there is no appreciable loss of microspheres from the microwells due to mechanical agitation even without a specific fixing technique. This effect is probably due to electrostatic forces between the microspheres and the optical fibers. These forces tend to bind the microspheres within the microwells. Thus, in most environments, it may be unnecessary to use any chemical or mechanical fixation for the microspheres.

2. Experimental

Figure 8:
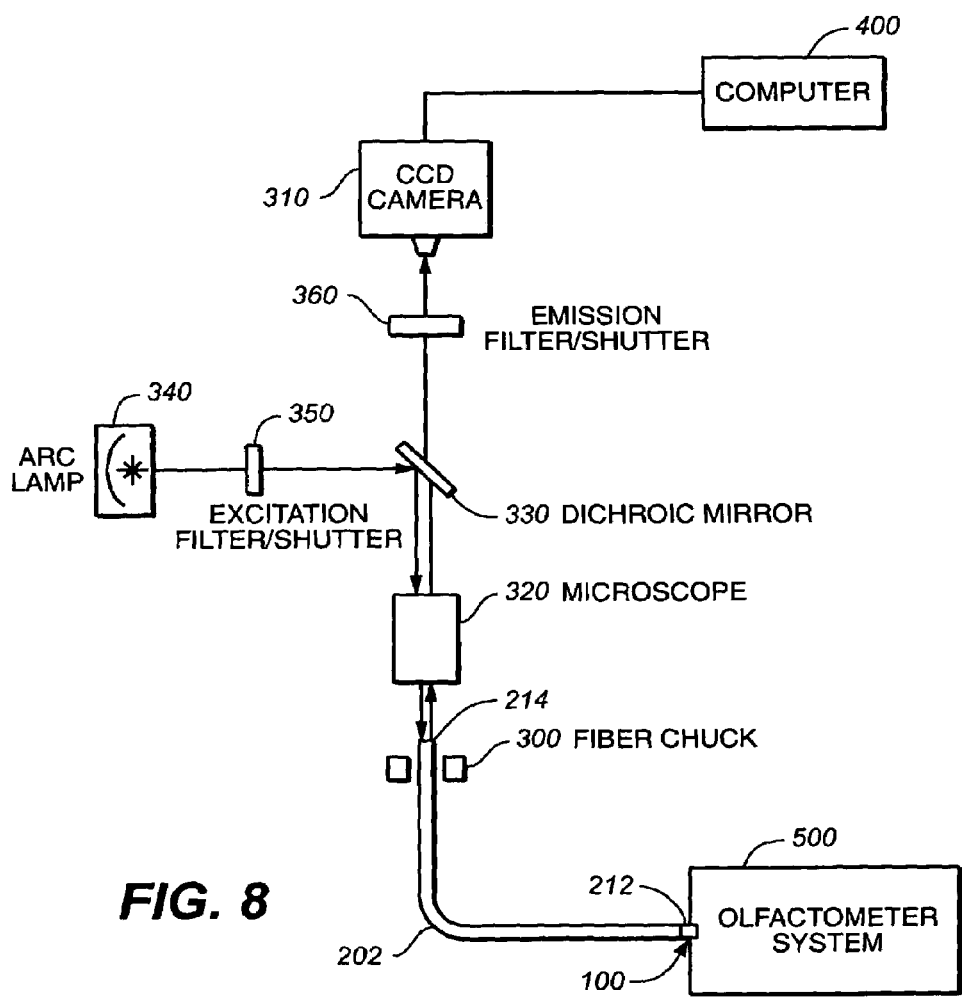
FIG. 8 is a schematic diagram illustrating the experimental apparatus used in the optical measurements of Examples 7 through 17.

Data Acquisition:

Characteristic temporal optical response data measurements of sensor bead and sensor array response to specific vapor analytes and excitation light energy were made according to the established method and instrumentation disclosed by White, et al., *Anal. Chem.* 68:2191–2202 (1996). In FIG. 8, a schematic diagram illustrates the experimental apparatus and instrumentation used for the data measurements reported in Examples 7 through 17.

In a typical measurement, the proximal end 214 of a fiber optic bundle 202 was placed into a fiber chuck 300 and secured for viewing with an Olympus microscope-based imaging system. In other embodiments, a conventional Olympus microscope slide platform and slide clamp was used for positioning alternative sensor array substrates, such as glass cover slips. An Olympus microscope 320 equipped with an epi-illuminator was utilized for optical measurements. The microscope 320 was equipped with Olympus 20× and 40× and Zeiss 100× objectives. An Omega 560 DCRP dichroic mirror 330 was used to direct filtered exitation light energy from a 75W Xenon arc lamp 340 to the sensor array 100 and to permit the emitted light energy, due to the characteristic optical response signature originating from each of the sensor beads 10 in the sensor array 100, to be recorded by a CCD frame transfer camera 310. The excitation light energy emanating from the arc lamp 340 was filtered by an Omega 535 BP40 integrated excitation light filter/shutter 350. The emission light energy which emitted from the sensor beads 10 of the sensor array 100 was filtered with an Omega 640 BP20 integrated emitted light filter/shutter 360 prior to the CCD frame transfer camera 310.

Experiments generally consist of collecting video camera frames of fluorescence response images of the characteristic optical response signatures of individual sensor beads in the sensor array 100 conveyed by the fiber optic bundle 202 to its proximal end 214. The bead and array images are recorded with a CCD frame transfer camera 310 (Model TE512EFT from Princeton Instruments, Trenton, N.J.). A preselected number of image frames are captured and sent to a computer system 400, comprising a Princeton Instruments NUBus camera interface card installed in a 8100AV Macintosh Power PC. Camera frame rates can be set at any desired value and typically range between 80 to 250 ms/frame. The following is a list of frame rates (time between data points) used in acquiring the data shown in for FIGS. 9–16. The specified frame rate corresponds to a specific time interval between data points.

Figure 9:
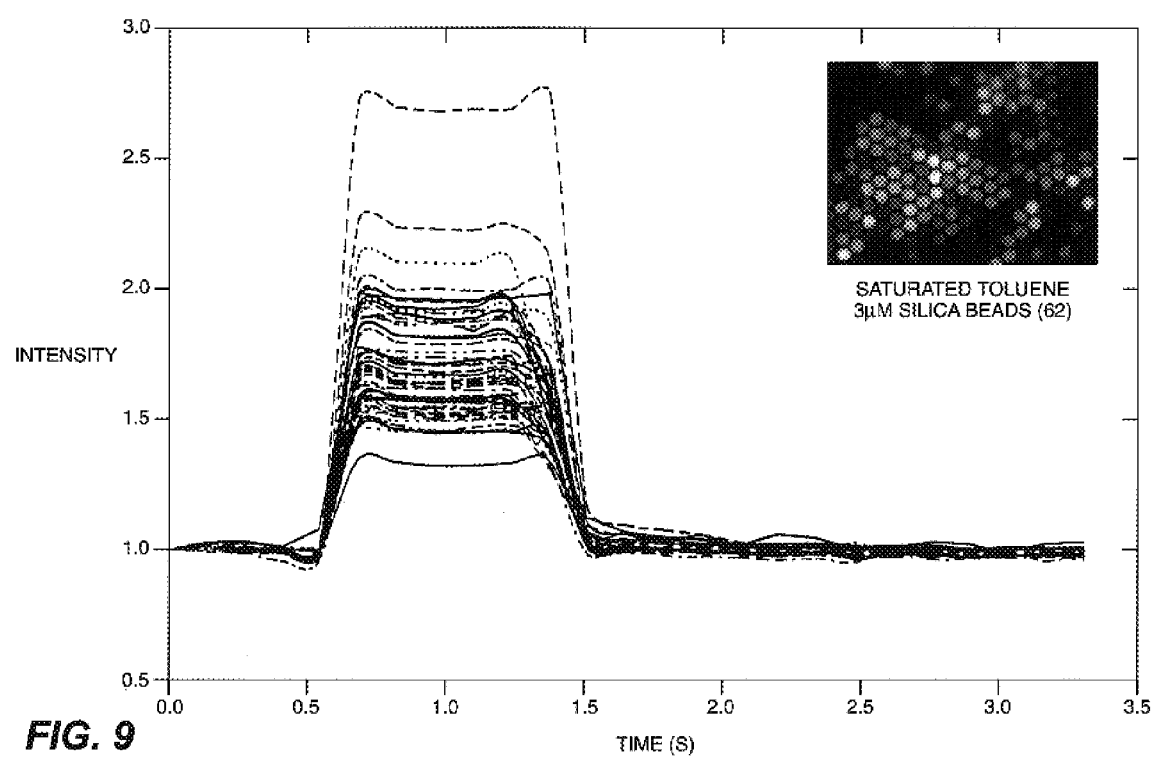
FIG. 9 illustrates the characteristic optical response signature of porous silica beads infiltrated with NILE RED dye upon exposure to toluene vapor.
Figure 10:
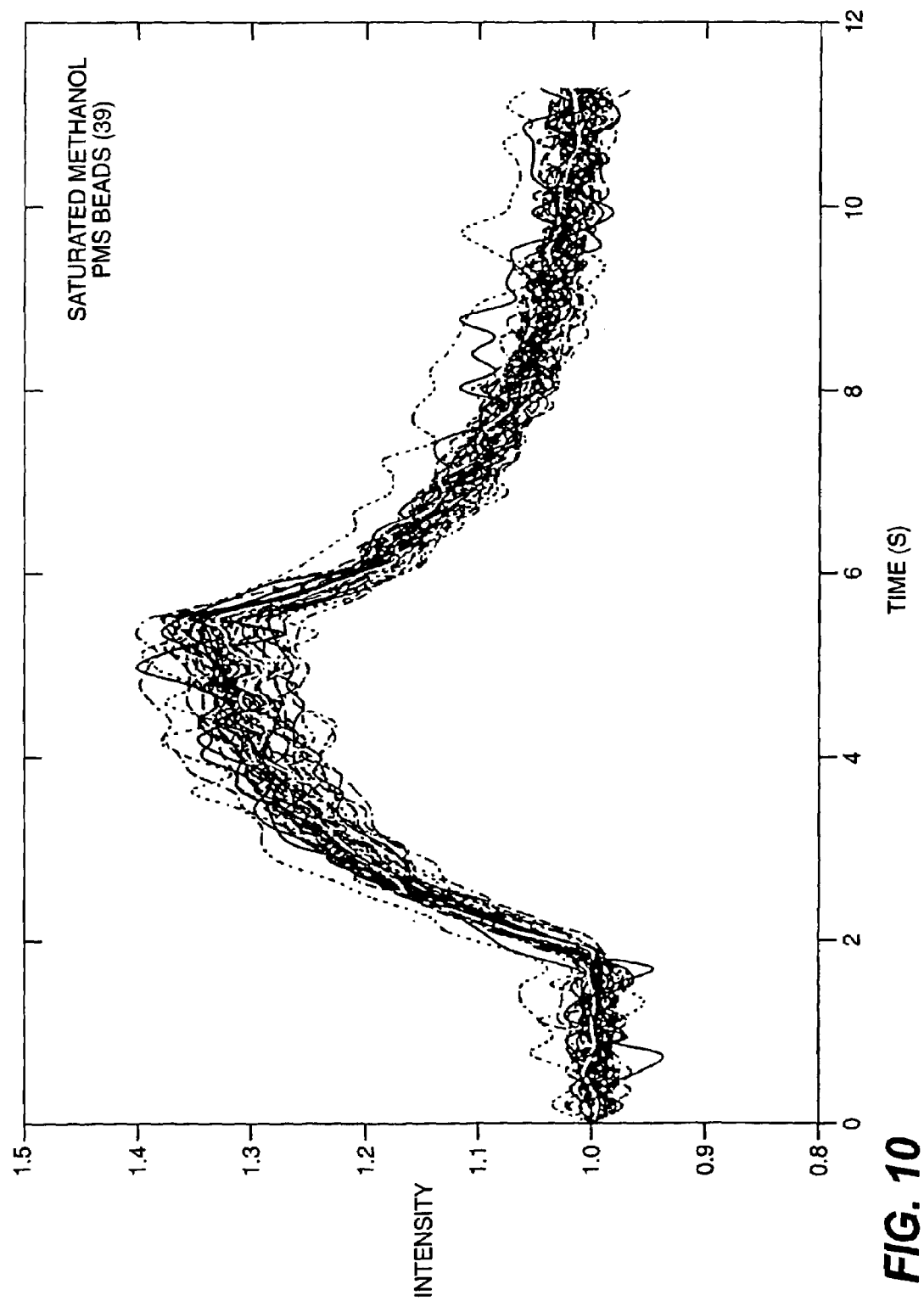
FIG. 10 illustrates the characteristic optical response signature of PMS beads infiltrated with NILE RED dye upon exposure to methanol vapor.
Figure 11A:
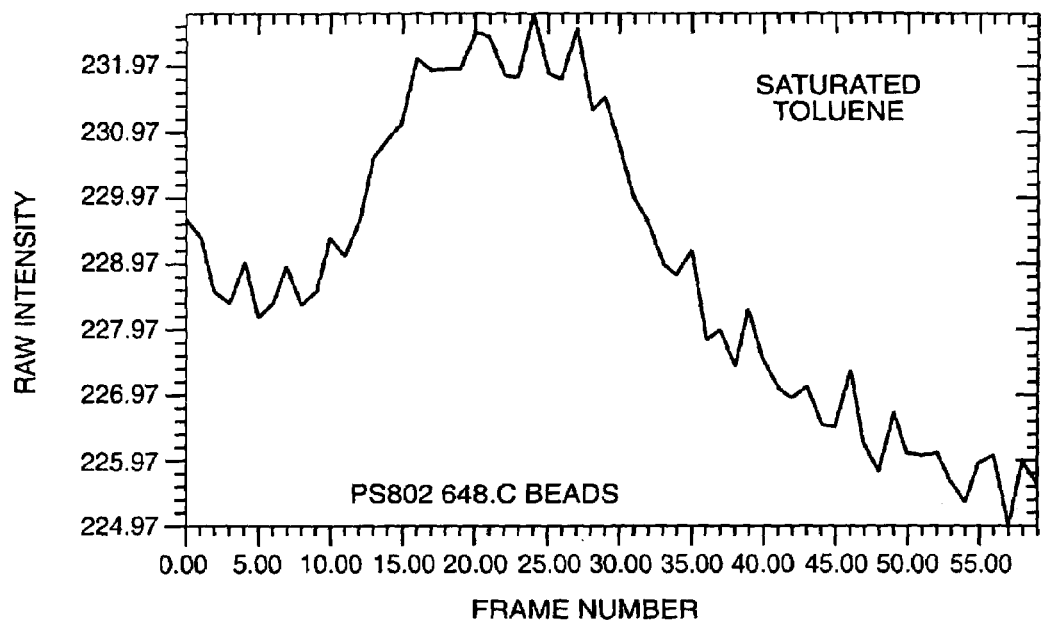
FIGS. 11A and 11B illustrate the characteristic optical response signature of a PS802 coated porous silica bead infiltrated with NILE RED dye upon exposure to toluene and methanol vapor.
Figure 11B:
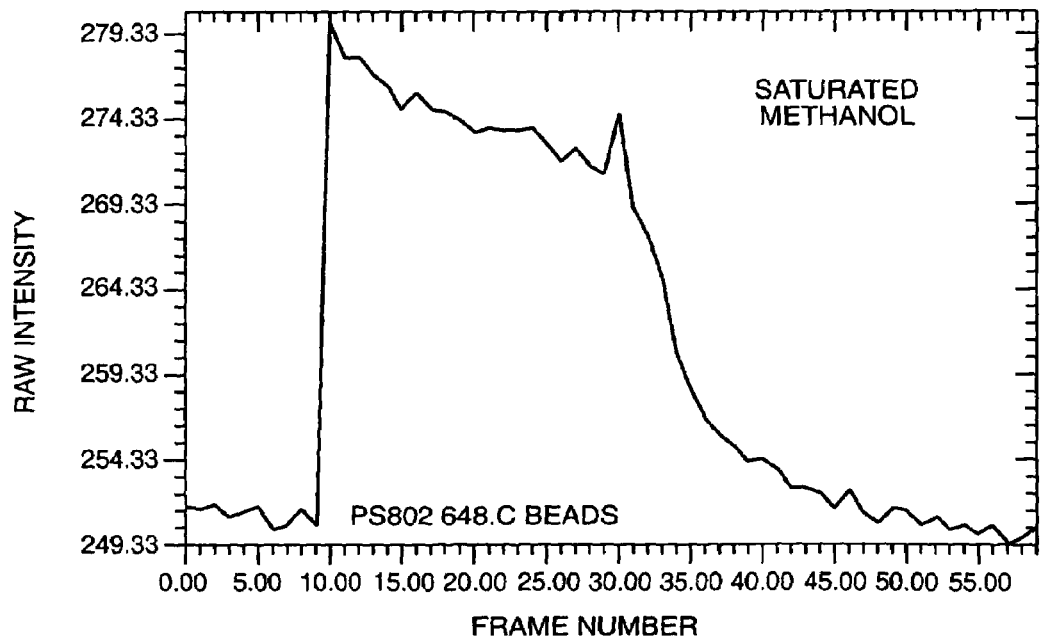
Figure 12A:
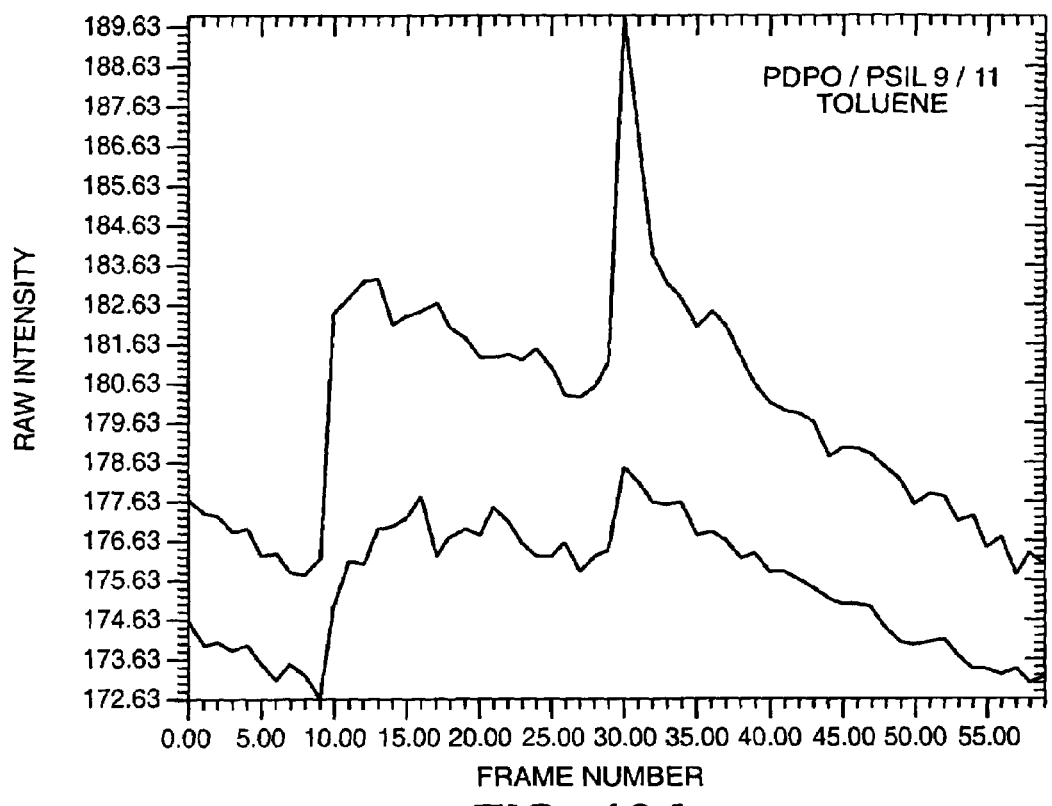
FIGS. 12A and 12B illustrate the characteristic optical response signature of a PDPO coated porous silica beads infiltrated with NILE RED dye upon exposure to toluene and methanol vapor.
Figure 12B:
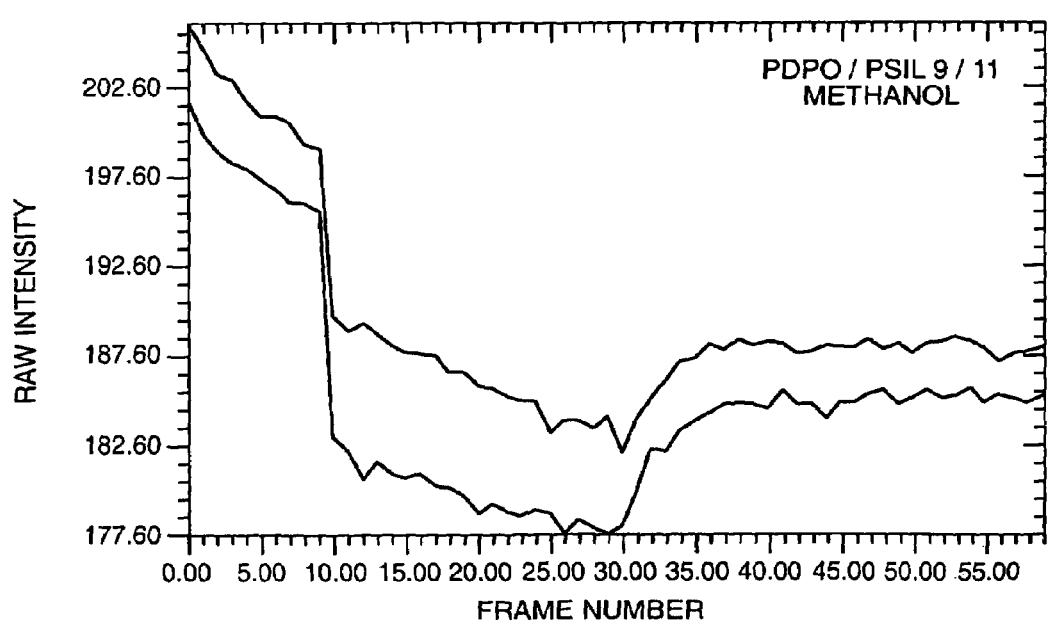
Figure 13:
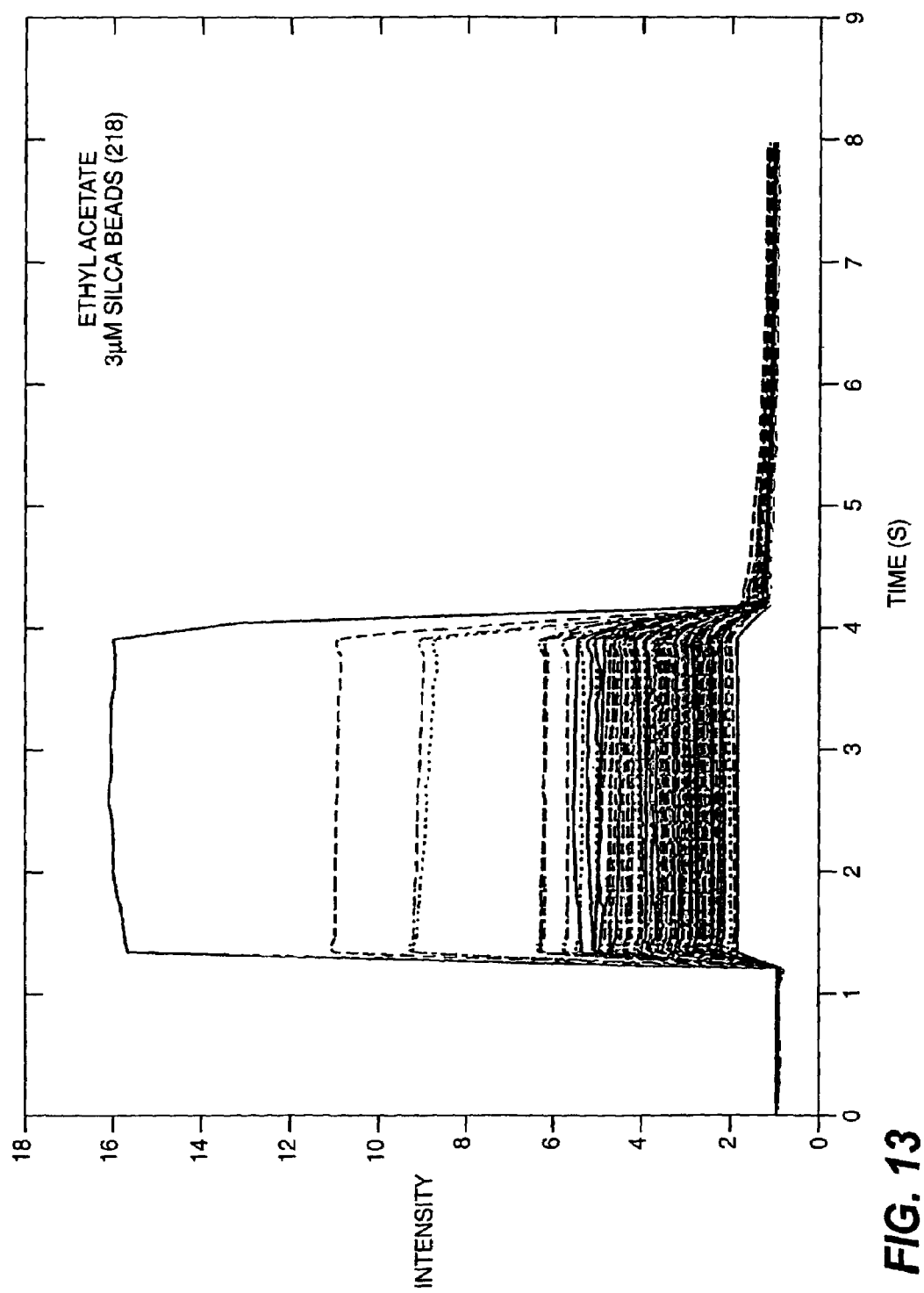
FIG. 13 illustrates the characteristic optical response signature of porous silica beads infiltrated with NILE RED dye upon exposure to ethyl acetate vapor.
Figure 14:
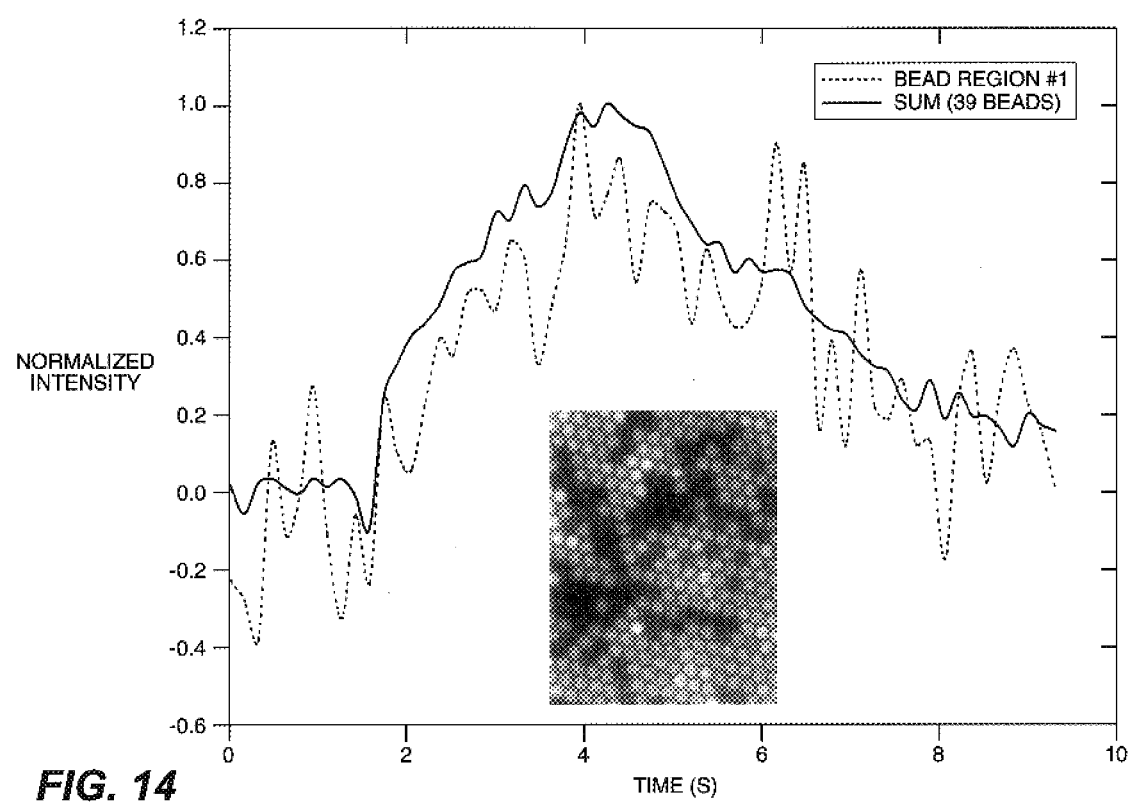
FIG. 14 illustrates the innovation of optical response signal summing for reducing signal-to-noise ratios in Nile Red infiltrated PMS bead subpopulation measurements of methanol vapor.
Figure 15:
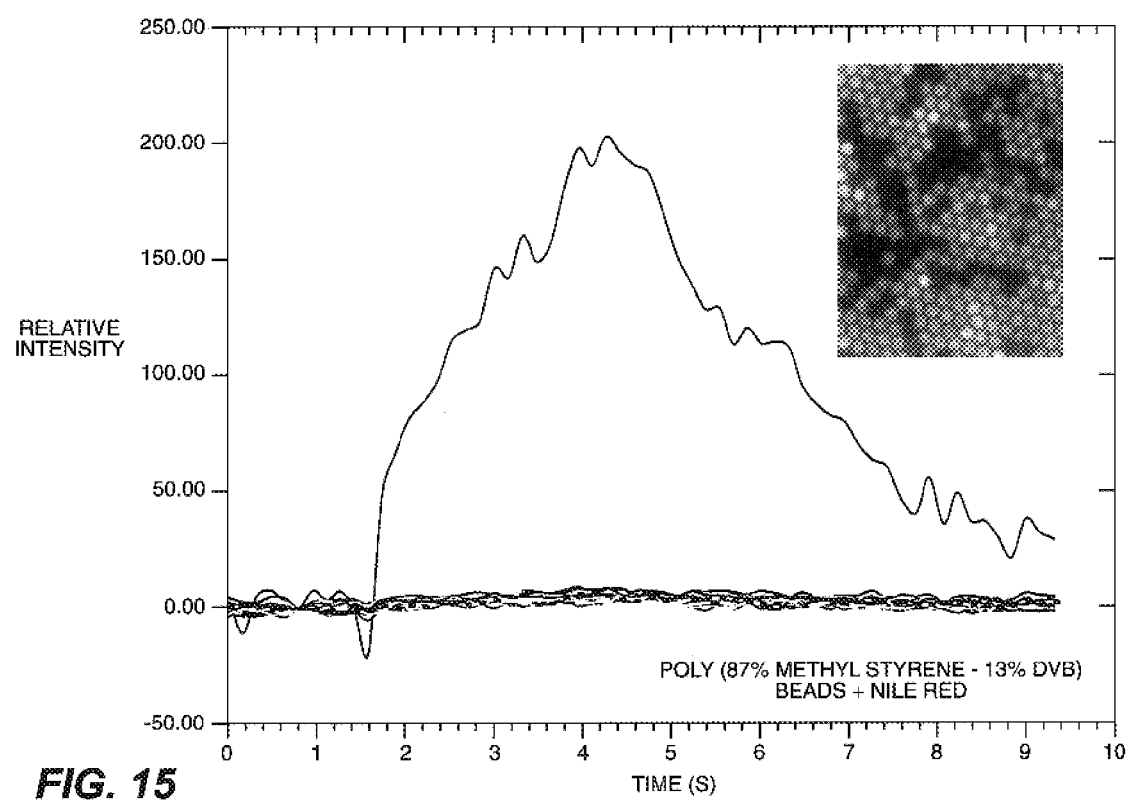
FIG. 15 illustrates the innovation of optical response signal summing for signal enhancement in PMS bead subpopulation measurements of methanol vapor.
Figure 16:
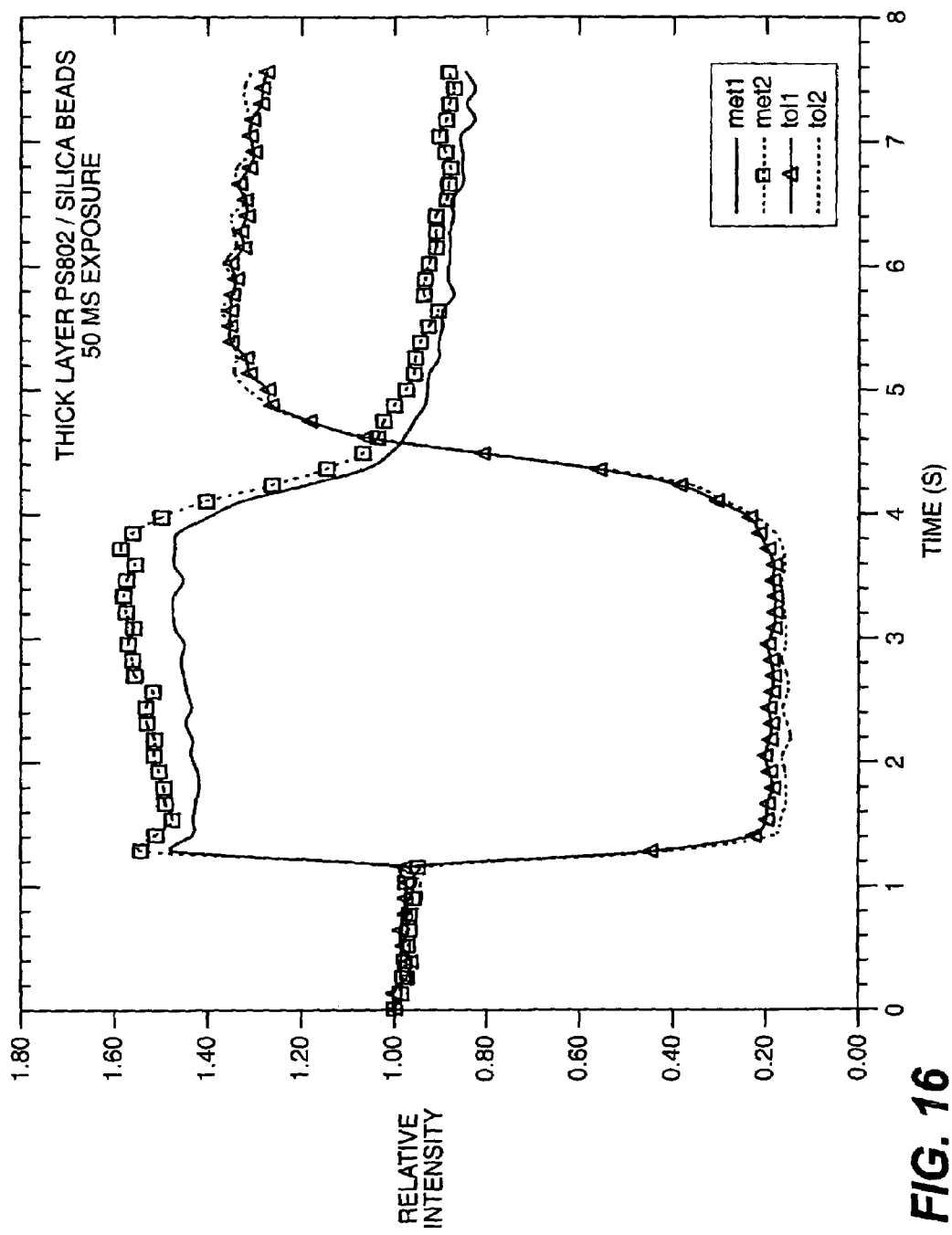
FIG. 16 compares the characteristic optical response signatures of two PS802 coated porous silica beads infiltrated with NILE RED dye upon exposure to toluene and methanol vapor.

| Figure | Rate (ms/frame) | Total No. of Frames |
| --- | --- | --- |
| FIG. 9 | 135 | 30 |
| FIG. 10 | 183.3 | 60 |
| FIG. 11 | 103.3 | 60 |
| FIG. 12 | 190.6 | 60 |
| FIG. 13 | 133 | 60 |
| FIG. 14 | 155 | 60 |
| FIG. 15 | 155 | 60 |
| FIG. 16 | 124 | 60 |

A conventional air dilution olfactometer and vacuum-controlled vapor delivery system 500, as commonly known and used in olfactory research and described in Kauer, et al., *J. Physiol.* 272:495–516 (1977), was used to apply controlled pulses of analyte vapor and air carrier gas to either a sensor bead substrate or the distal end 212 of a fiber optic sensor array 100 containing an array of sensor beads 10 immobilized in microwells 250.

To produce a saturated vapor sample, generally, a stream of air carrier gas is passed through a 5 mL cartridge containing filter paper saturated with the analyte. Analyte dilutions are produced by adjusting the relative flow rates of saturated vapor and clean carrier gas streams. Typically, a flow rate of 100 mL/min is used for the combined gas flow to the sensor array. At this flow rate, a 2 second pulse would deliver approximately 3.3 mL of analyte vapor with carrier gas. In generally, depending on the analyte vapor pressure and dilution factor, vapor pulses contain between $10^{-7}$ to $10^{-5}$ mol of analyte.

The vapor pulse was typically delivered during the 11th through 30th frame, commencing on the 11 th frame. The duration of the vapor pulse varied with the specific frame rate utilized and typically ranged between 2 to 3 seconds. Baseline control measurements were performed with high purity, Ultra Zero grade air. The air pulse measurements were performed to account for any bead responses due to the vapor carrier gas.

Data Processing:

Following the collection of a temporal series of sensor bead or sensor array images, segments are drawn, using IPLab image processing software (Signal Analytics, Vienna, Va.), over each pixel which corresponds to an individual fiber where the fiber is coupled to one sensor bead at its distal end. The mean fluorescence intensity was measured for each one of these segments in each frame in the sequence. This is done for both the vapor pulse responses and the baseline air pulse responses. Averages of multiple runs of each may be performed to improve data quality where needed. The air pulse data is then subtracted from the vapor pulse data to subtract the background due to air alone. The resulting data can be plotted to yield temporal intensity responses for all beads of interest. In a preferred embodiment, the sensor array data are used in a neural network analysis according to the method disclosed in White, et al, *Anal. Chem.* 68:2193–2202 (1996).

All data manipulation is performed within the IPLab program environment using simple operator scripts that call standardized image or data processing routines included with the software. These scripts and routines consist of a data collection portion and a data analysis portion.

In the data collection portion, there are three segments or loops as follows:

Loop 1. This establishes the baseline fluorescence of each sensor. This loop can be shortened or extended to adjust to slower or faster response times of specific sensor beads or sensor arrays to certain analytes. For Examples 7 through 17, this loop was set between 5 to 10 frames.

Loop 2. This is the vapor exposure loop. A vapor pulse is applied just before this loop starts by way of a script command that sends a 5 volt pulse to an attached solenoid valve which switches a vacuum line off, thereby allowing a vapor sample to emit from the end of a nozzle. Typically, this loop is 20 frames in duration. In Example 7, a 10 frame duration was utilized.

Loop 3. This is a sensor recovery loop. Another 5 volt trigger pulse is sent to a solenoid which switches back to its initial position, causing the vacuum system to resume collection of the solvent vapor and carry it off to waste. Typically, this loop is of 30 frames duration. In Example 7, a 15 frame duration was utilized.

Data Analysis:

In the data analysis portion, pre-selected segments taken from a previously collected "focus" image are transferred to the sequence of images collected. These segments, drawn by the user, allow the mean pixel intensity to be measured in particular regions throughout the image field. Typically, they are drawn over individual pixels of a fiber optic sensor array, each of which contains a bead. The script then enters a loop that steps through each frame, measuring the mean pixel intensity within each segment, and placing the values in data columns. The resulting columns can then be plotted to yield the temporal response of each bead of interest. Before plotting, however, responses are "standardized" by dividing the data for each bead response by its first point. Thus, all responses can be normalized to start at a value of 1.0.

Bead Response Summing:

The optical response signals from a large number of sensor beads within each bead subpopulation can be summed by simply adding the baseline-adjusted intensity values of all responses at each time point, generating a new temporal response comprised of the sum of all bead responses. Signal summing can be performed in real time or during post-data acquisition data reduction and analysis. In one embodiment, signal summing is performed with a commercial spreadsheet program (Excel, Microsoft, Redmond, Wash.) after optical response data is collected. In a typical procedure, the standardized optical responses are adjusted to start at a value of 0.0 by subtracting the integer 1.0 from all data points. Doing this allows the baseline-loop data to remain at zero even when summed together and the random response signal noise is canceled out. The vapor pulse-loop temporal region, however, exhibits a characteristic change in response, either positive, negative or neutral, prior to the vapor pulse and often requires a baseline adjustment to overcome noise associated with drift in the first few data points due to charge buildup in the CCD camera. If no drift is present, tyically the baseline from the first data point for each bead sensor is subtracted from all the response data for the same bead. If drift is observed, the average baseline from the first ten data points for each bead sensor is substracted from the all the response data for the same bead. By applying this baseline adjustment, when multiple bead responses are added together they can be amplified while the baseline remains at zero. Since all beads respond at the same time to the vapor pulse, they all see the pulse at the exact same time and there is no registering or adjusting needed for overlaying their responses. Cummulative response data is generated by simply adding all data points in successive time intervals. This final column, comprised of the sum of all data points at a particular time interval, may then be compared or plotted with the individual bead responses to determine the extent of signal enhancement or improved signal-to-noise ratios as shown in FIGS. 14 and 15.

EXAMPLE 1

Preparation of Porous Silica NILE RED Dye Beads:

Approximately 0.5 cm$^3$ of nominally 3.2 micro meters diameter commercial porous silica beads were removed from a LUNA column (Phenomenex, Torrance, Calif.). Sample of beads were placed onto a filter paper and, using vacuum filtration, 0.5 mL of NILE RED dye (Eastman Kodak, Rochester, N.Y.) solution (1 mg/mL in toluene) was poured over beads. NILE RED dye was immediately taken up by silica beads, turning them a deep purple color. The beads were washed repeatedly with toluene to remove any excess, non-adsorbed NILE RED dye. The beads were dried on a watch glass overnight. Beads were then placed into microwells formed by etching a fiber optic bundle according to the method of the present invention.

EXAMPLE 2

Preparation of PDPO Polymer Coated Porous Silica Beads:

A silanizing solution was prepared from 20 μL N-octadecyl-triethyoxysilane in 980 μL of ethanol/water (95% ethanol, 5% ultrapure water with pH adjusted to 4.9 with acetic acid). The LUNA porous silica beads of Example 1 were dispersed in an excess of silanizing solution for approximately 10 minutes, vortexing continuously. The particles were rinsed three times with ethanol and dried in a 120° C. oven, overnight for approximately 12 hours.

Stock solution of PDPO, poly(2,6-dimethyl-1,4-phenylene oxide),(Aldrich, Milwaukee, Wis.) and Nile Red was prepared from 0.09 g PDPO and 1.0 mL chloroform. After complete dissolution of the polymer, a 100 μL aliquot of 1 mg/mL NILE RED dye in chloroform was added. The resultant solution was vortexed continuously for uniform dispersion.

Excess PDPO/NILE RED dye was added to a small fraction of the silanized porous beads, approximately 100 μL polymer/dye solution to approximately 1 mg of beads. The sample was vortexed for approximately 3 hours then washed. Excess polymer dye was removed and the beads were then washed repeatedly with methylene chloride, two to three times, followed by a washing with 0.01% polyoxyethylene-sorbitan monolaurate, TWEEN 20 detergent (J. T. Baker, Cleveland, Ohio), in water. The washed beads were collected in a solution of 0.01% TWEEN 20 detergent/ultrapure water. A single, small drop was placed on a microscope coverslip and allowed to dry protected from light.

EXAMPLE 3

Preparation of Non-Porous Silica/NILE RED Dye Beads Coated With Polysiloxane Polymer:

Commercially available non-porous 3.1 Nm silica beads (Bangs Laboratory, Fishers, Ind.) were first silanized in excess silanizing solution, a 10% solution by volume of 3-(trimethoxysilyl)propyl methacrylate (Aldrich, Milwaukee, Wis.) in acetone, overnight. Excess silanizing solution was decanted and the beads were rinsed repeatedly, two to three times, with ultrapure acetone, vortexing and centrifuging between washes. The beads were soaked in excess NILE RED dye solution (1 mg/ml in toluene) for approximately 3 hours while vortexing so as to fully saturate the surface. The bead solution was centrifuged and excess dye solution was decanted. A mixture of 7.9 mg benzoin ethyl ether (Polysciences Inc., Warrington, Pa.), 250 microliters stock Ni RED dye in toluene and 250 microliters (15–20% acryloxypropyl-methylsiloxane) 80–85% dimethylsiloxane copolymer (Gelest Inc., Tullytown Pa.) were then added to the beads. The bead suspension was vortexed to uniformly coat the particles. The resultant suspension mixture was added dropwise to approximately 100 mL 0.1% TWEEN 20 detergent in ultrapure water stirring at approximately 350 revolutions per munute (rpm). Polymerization was accomplished by ultraviolet excitation for 10 second durations for a total exposure of 30 seconds. The sample solution was stirred over night. The suspension was passed through a 230 micrometer sieve, followed by a 5 μm sieve. The filtrate was centrifuged at 3000 rpm for approximately 5 minutes and the beads were collected into centrifuge tubes and washed with 0.01% TWEEN 20 detergent in ultrapure water. A single small drop was placed on a microscope coverslip and allowed to dry protected from light.

EXAMPLE 4

Preparation of (15–20% Acryloxypropylmethylsiloxane) 80–85% Dimethylsiloxane Copolymer Beads with nile red:

Approximately 25 mL of ultrapure water plus 25 mL ethanol were placed in a 100 mL round bottom flask and stirred with a stirbar at approximately 350 rpm. A mixture of 500 μL (15–20% acryloxypropylmethylsiloxane) 80–85% dimethylsiloxane copolymer, 200 μL NILE RED dye solution (1 mg/mL in chloroform) and 250 μL methylene chloride was made and added dropwise to the stirred water/ ethanol solution. A solution of 5.5 mg AIBN, N,N'-azobis-isobutyl nitrile (2,2'-azobis-2-methylproprio-nitrile)(Phaltz & Bauer, Inc.), in methylene chloride was added to the stirring dispersion. The mixture was degassed with argon for approximately one hour and then heated to approximately 70 degrees celcius. After approximately three hours of heating, 20 mL of 0.01% TWEEN 20 detergent in ultrapure water was added to the mixture. Heating and stirring was continued for approximately 12 hours. The mixture was passed through 230 micrometer sieve, then solids collected from centrifugation at up to 5000 rpm. The solids were washed twice with methanol and then washed with 0.01% TWEEN 20 detergent in ultrapure water. The resultant beads were collected in a solution of 0.01% Tween 20 in ultrapure water. A single drop of the bead suspension was placed on a microscope coverslip and allowed to dry protected from light.

EXAMPLE 5

NILE RED Dye Dyed Poly(Methylstyrene/Divinyl Benzene) Beads:

pproximately 1 mg of commercially available 3.15 μm polymer beads, 87% methyl styrene, 13% divinyl benzene with amine functionalized surface (Bangs Laboratories, Fishers, Ind.), was washed in 1 mL of methanol by vortexing, centrifuging at approximately 3000 rpm and decanting the solvent. The beads were transferred to brown vial and approximately 100 μL of NILE RED dye solution (1 mg/mL in toluene) was added. The sample was vortexed and placed on a wrist shaker to agitate overnight. The suspension was transferred to a microcentrifuge tube and washed with methanol until the decanted solvent was clear. The beads were collected in approximately 0.5 mL of a solution of 0.01% TWEEN 20 detergent in ultrapure water. A single drop placed on a microscope coverslip and allowed to dry protected from light.

EXAMPLE 6

Plasticizer Modified Poly(Methylstyrene/Divinyl Benzene) Beads With NILE RED Dye Incorporated:

Approximately 1 mg of commercially available 3.15 μm polymer beads, 87% methyl styrene, 13% divinyl benzene with amine functionalized surface (Bangs Laboratories, Fishers, Ind.), were rinsed with methanol according to Example 5 and transferred to a brown vial. Approximately 2–40% (w/w) plasticizer to polymer solutions of plasticizers, tritolyl phosphate (TTP), triphenyl phosphate (TPP), and dibutyl phthalate (DBP) (Aldrich, Milwaukee, Wis.), with NILE REd dye solution (1 mg/mL in toluene) were added to samples of beads, covered, vortexed then shaken on wrist shaker for approximately 12 hours. The beads were transferred to microcentifuge tubes and washed with NILE RED dye in methanol, then repeatedly with methanol until the decanted solvent was clear. The beads were collected in a solution of 0.01% TWEEN 20 detergent in ultrapure water. A single drop of the suspension was placed on a microscope coverslip and allowed to dry protected from light.

EXAMPLE 7

The porous silica beads prepared by the method of Example 1 were evaluated to determine their characteristic optical response signature to toluene vapor following the experimental method described above. The results are presented in FIG. 9 where the temporal optical response of 62 individual bead sensors to a pulse of toluene vapor is shown.

EXAMPLE 8

The poly(methylstyrene/divinyl benzene) beads prepared by the method of Example 5 were evaluated to determine their characteristic optical response signature to methanol vapor. The results are presented in FIG. 10 where the temporal optical response of 39 individual bead sensors to a pulse of methanol vapor is shown.

EXAMPLE 9

The (15–20% acryloxypropylmethylsiloxane) 80–85% dimethylsiloxane copolymer beads prepared by the method of Example 4 were evaluated to determine their characteristic optical response signature to both toluene and methanol vapor. The results are presented in FIGS. 11A and 11B where the temporal optical responses of an individual bead sensor to a pulse of toluene and a pulse of methanol vapor is shown.

EXAMPLE 10

The PDPO polymer coated porous silica beads prepared by the method of Example 2 were evaluated to determine their characteristic optical response signature to both toluene and methanol vapor. The results are presented in FIGS. 12A and 12B where the temporal optical responses of an individual bead sensor to a pulse of toluene and a pulse of methanol vapor is shown.

EXAMPLE 11

Porous silica beads prepared by the method of Example 1 were incorporated into etched microwells on the distal end of a fiber optic bundle according to the method described above.

The resultant sensor array was evaluated to determine the characteristic optical response signature of the bead sub-population to ethyl acetate vapor. The results are presented in FIG. 13 where the temporal optical response of 218 individual bead sensors to a pulse of ethyl acetate vapor is shown.

EXAMPLE 12

The signal summing method of the present invention was evaluated in analyzing the experimental measurements made on poly(methylstyrene/divinyl benzene) beads prepared by the method of Example 5 and tested by the method of Example 8. The results are shown in FIG. 14 where the normalized temporal optical response for a single sensor bead, Bead #1, is compared with the summed responses of all 39 beads tested. As shown by FIG. 14, the signal summing method of the present invention significantly reduces the experimental noise encountered in a single sensor bead measurement and provides a substantial improvement, ten-fold or greater, in the signal-to-noise ratio of analytical measurements.

EXAMPLE 13

The signal summing method of the present invention was evaluated in analyzing the experimental measurements made on poly(methylstyrene/divinyl benzene) beads prepared by the method of Example 5 and tested by the method of Example 8. The results are shown in FIG. 15 where the actual relative intensities of the temporal optical response for each of the 39 sensor beads is compared to relative intensity of the temporal optical response obtained from signal summing. As shown by FIG. 15, substantial signal enhancement is obtained by signal summing with a correspondingly significant improvement, up to a hundred fold, in the detection limit for target analytes.

EXAMPLE 14

The polysiloxane coated porous silica beads prepared by the method of Example 3 were evaluated to determine their characteristic optical response signature to both toluene and methanol vapor. The results are presented in FIG. 16 where the temporal optical responses of two bead sensors to both toluene and methanol are shown. The results shown in FIG. 16 demonstrates the capability of this subpopulation of bead sensors to distinguish between two analytes of interest by utilizing the characteristic optical response signatures of the bead sensors to specific analytes.

EXAMPLE 15

Figure 17:
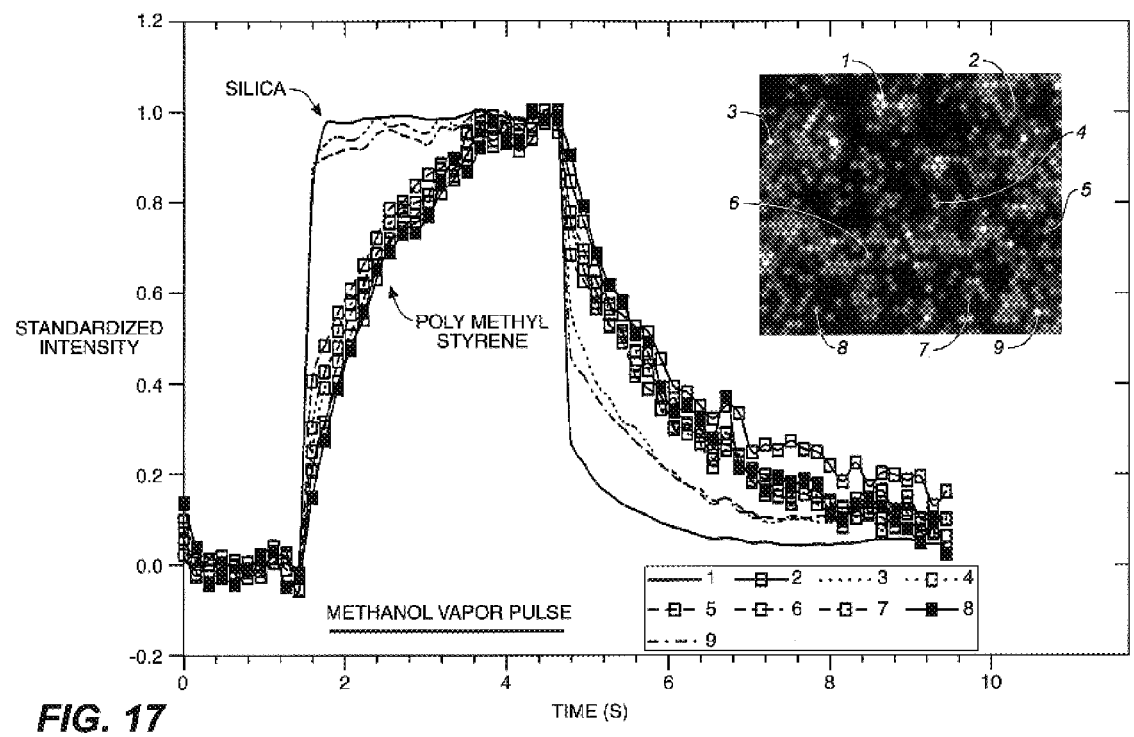
FIG. 17 compares the characteristic optical response signatures to methanol vapor which are used for decoding NILE RED dye infiltrated porous silica and PMS bead subpopulations in a self-encoded fiber optic sensor array of the present invention.

A 50/50 mixture of porous silica beads prepared by the method of Example 1 and poly(methylstyrene/divinyl benzene) beads prepared by the method of Example 5 were randomly dispersed and incorporated into etched microwells on the distal end of a fiber optic bundle according to the method of the present invention as described above. The resultant sensor array was evaluated to determine the characteristic optical response signature of the bead subpopulation to methanol vapor. An 535 nm excitation filter and 600 nm emission filter was used in this experiment. The results are presented in FIG. 17 where the normalized temporal optical response of 3 porous silica bead sensors and 6 PMS bead sensors to a pulse of methanol vapor is shown. In this example, the characteristic emitted light peak shapes of the bead subpopulations provide a distinguishable characteristic response signature for each subpopulation. FIG. 17 demonstrates the innovative self-encoding feature of the present invention where the identity and location of the beads is determined in a single measurement of a reference vapor analyte.

EXAMPLE 16

Figure 18:
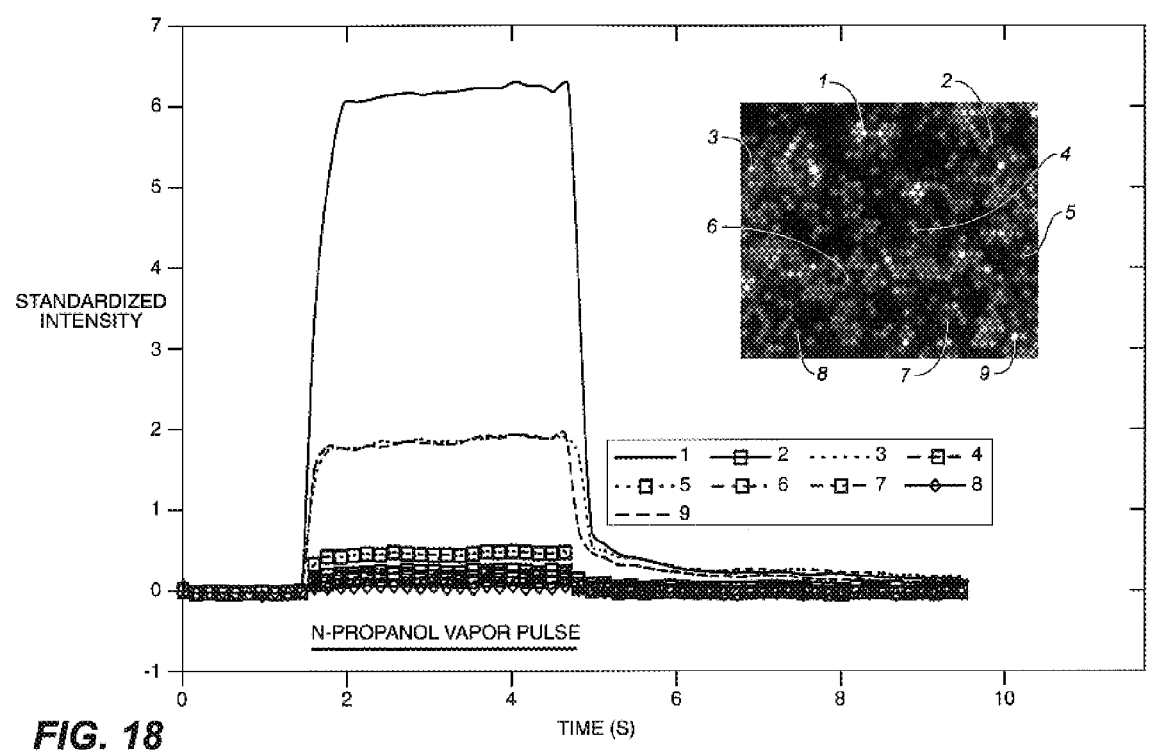
FIG. 18 compares the characteristic optical response signatures of NILE RED dye infiltrated porous silica and PMS bead subpopulations to n-proponal vapor in a self-encoded fiber optic sensor array of the present invention.

The self-encoded fiber optic sensor array produced by the method of Example 15 was evaluated by measuring the characteristic temporal optical response signature of the porous silica and PMS sensor bead subpopulations of the array in response to a pulse of n-propanol vapor. The results are presented in FIG. 18 where the temporal optical response of 3 porous silica bead sensors and 6 PMS bead sensors to a pulse of n-propanol vapor is shown. In this example, the characteristic emitted light intensities of the bead subpopulations provide a distinguishable characteristic response signature for each subpopulation. FIG. 18 demonstrates the advantages of using the distinct characteristic temporal optical response signature of different bead subpopulations to detect a specific analyte of interest. Note that the identity and location of the bead sensors in the sensor array was decoded by the method of Example 15. By the combination of self-encoding the sensor array by the method of Example 15 and the sensor array measurement made by the method of the current Example 16, the sensor array was trained to detect and distinguish methanol from n-propanol.

EXAMPLE 17

Figure 19:
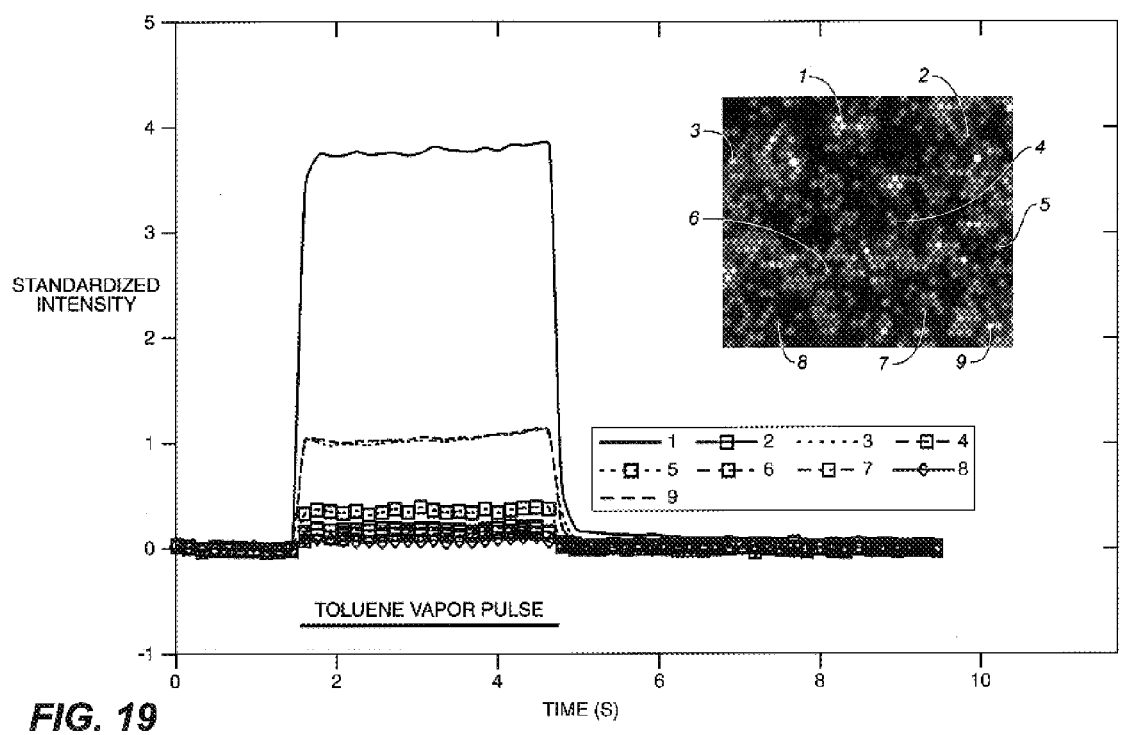
FIG. 19 compares the characteristic optical response signatures of NILE RED dye infiltrated porous silica and PMS bead subpopulations to toluene vapor in a self-encoded fiber optic sensor array of the present invention.

The self-encoded fiber optic sensor array produced by the method of Example 15 was evaluated by measuring the characteristic temporal optical response signature of the porous silica and PMS sensor bead subpopulations of the array in response to a pulse of toluene vapor. The results are presented in FIG. 19 where the temporal optical response of 3 porous silica bead sensors and 6 PMS bead sensors to a pulse of toluene vapor is shown. FIG. 19 demonstrates the advantages of using the characteristic temporal optical response signature of different bead subpopulations to detect a specific analyte of interest. Note that the identity and location of the bead sensors in the sensor array was decoded by the method of Example 15. By the combination of decoding the self-encoding the sensor array by the method of Example 15, the sensor array measurement made by the method of Example 16, and the sensor array measurement made by the method of the current Example 17, the sensor array was trained to detect and distinguish between the group of target analytes comprising methanol, n-propanol, and toluene.

EXAMPLE 18

Figure 20:
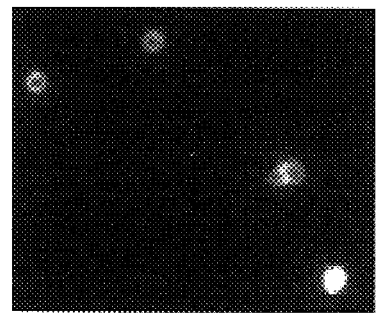
FIG. 20 compares the differences in bead swelling response of PS802 coated porous silica, poly methyl styrene, and poly methyl styrene/divinyl benzene bead subpopulations upon exposure to toluene vapor.
Figure 20:
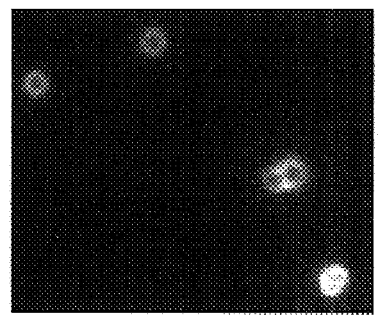
Figure 20:
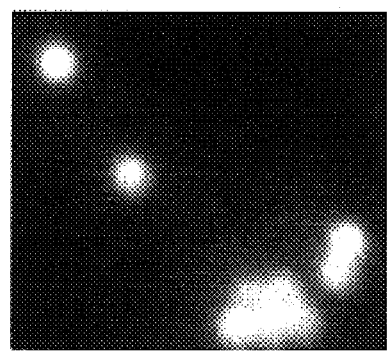
Figure 20:
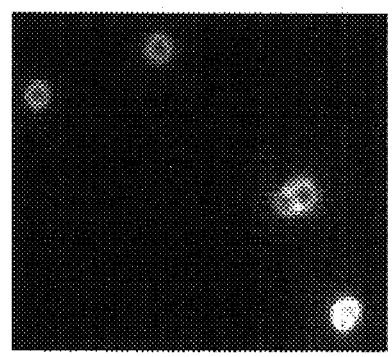
Figure 20:
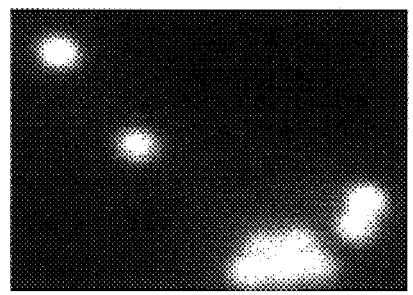
Figure 20:
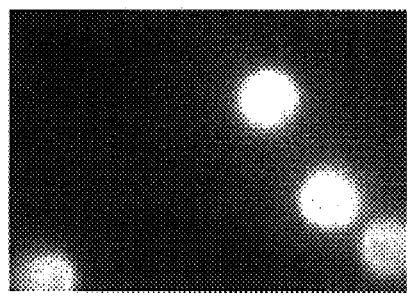

Samples of PS802 bead sensors produced by the method of Example 4, Poly methyl styrene/2% divinyl benzene bead sensors produced by the method of Example 5, and commercially available poly methyl styrene beads (Bangs Laboratory, Fishers, Ind.) were dispersed on a microscope coverslip substrate. Following equilibration of each bead subpopulation in air, each subpopulation was exposed to a pulse of saturated toluene vapor while illuminating the beads with excitation light energy. The changes in bead dimension due to the swelling response of each polymer type to toluene vapor was monitored using the apparatus of FIG. 7. The response of the bead was recorded by filming the time varying fluorescence image of the beads and capturing changes in bead image dimensions with a CCD camera. FIG. 20 illustrates the differences in swelling response of the three bead subpopulations by comparing the initial fluorescence image of each bead type in air with subsequent image of each bead type following exposure to toluene vapor. Such measurements of the swelling response characteristics of various polymer candidate materials is useful in prescreening bead sensor materials for use as bead sensor elements in the self-encoded sensor array of the present invention.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An assay method comprising:
 a) providing a sensor array comprising:
  i) a first subpopulation comprising first sensor element, and
  ii) a second subpopulation comprising second sensor elements;
 b) adding a sample comprising a first target analyte that binds to said first sensor elements;
 c) measuring
  i) a first fluorescent signal of a first of said first sensor elements; and
  ii) a second fluorescent signal of a second of said first sensor elements; and
 d) summing said first and second fluorescent signals.

2. A method according to claim 1 further comprising:
 b) adding a sample comprising a second target analyte that binds to said second sensor elements;
 c) measuring
  i) a third fluorescent signal of a first of said second sensor elements; and
  ii) a fourth fluorescent signal of a second of said second sensor elements; and
 d) summing said third and fourth fluorescent signals.

3. A method according to claim 1 wherein said first and second sensor elements comprise beads.

4. A method according to claim 1 wherein said sensor array comprises beads distributed in wells.

5. A method according to claim 1 wherein said first and second sensor elements comprise chemical functional groups.

6. A method according to claim 1 wherein said first and second sensor elements comprise oligonucleotides.

7. A method according to claim 1 wherein said first target analyte is an oligonucleotide.

8. A method according to claim 1 wherein prior to said summing, the baseline of said first and second fluorescent signals are adjusted.

9. A method according to claim 1 wherein the signal-to-noise ratio is increased as a result of said summing.

10. A method according to claim 1 wherein said sensor array comprises a fiber optic bundle.

* * * * *